US011634427B2

(12) United States Patent
Iwasaki et al.

(10) Patent No.: US 11,634,427 B2
(45) Date of Patent: Apr. 25, 2023

(54) CRYSTAL NUCLEATING AGENT FOR POLYOLEFIN RESIN, METHOD FOR PRODUCING CRYSTAL NUCLEATING AGENT FOR POLYOLEFIN RESIN, AND METHOD FOR IMPROVING FLUIDITY OF CRYSTAL NUCLEATING AGENT FOR POLYOLEFIN RESIN

(71) Applicant: NEW JAPAN CHEMICAL CO., LTD., Kyoto (JP)

(72) Inventors: Shohei Iwasaki, Kyoto (JP); Yohei Uchiyama, Kyoto (JP); Kazuya Matsumoto, Kyoto (JP); Mitsuko Inoue, Kyoto (JP); Yurie Shinoda, Kyoto (JP); Takayuki Maeda, Kyoto (JP)

(73) Assignee: NEW JAPAN CHEMICAL CO., LTD., Kyoto (JP)

( * ) Notice: Subject to any disclaimer, the term of this patent is extended or adjusted under 35 U.S.C. 154(b) by 241 days.

(21) Appl. No.: 16/321,775

(22) PCT Filed: Jul. 21, 2017

(86) PCT No.: PCT/JP2017/026379
§ 371 (c)(1),
(2) Date: Jan. 29, 2019

(87) PCT Pub. No.: WO2018/021161
PCT Pub. Date: Feb. 1, 2018

(65) Prior Publication Data
US 2020/0325150 A1 Oct. 15, 2020

(30) Foreign Application Priority Data

Jul. 29, 2016 (JP) ................................ 2016-149528
Jun. 30, 2017 (JP) ............................ JP2017-128572

(51) Int. Cl.
| | | |
|---|---|---|
| *C07D 493/04* | (2006.01) | |
| *C08K 5/1575* | (2006.01) | |
| *C08K 5/30* | (2006.01) | |
| *C08K 5/098* | (2006.01) | |
| *C08K 5/527* | (2006.01) | |
| *C08K 5/20* | (2006.01) | |
| *B29B 9/06* | (2006.01) | |
| *B29C 45/00* | (2006.01) | |
| *B29K 23/00* | (2006.01) | |
| *B29K 105/00* | (2006.01) | |

(52) U.S. Cl.
CPC ............ *C07D 493/04* (2013.01); *C08K 5/098* (2013.01); *C08K 5/1575* (2013.01); *C08K 5/20* (2013.01); *C08K 5/527* (2013.01); *B29B 9/06* (2013.01); *B29C 45/0001* (2013.01); *B29K 2023/00* (2013.01); *B29K 2105/0047* (2013.01)

(58) Field of Classification Search
None
See application file for complete search history.

(56) References Cited

U.S. PATENT DOCUMENTS

| | | | | |
|---|---|---|---|---|
| 4,314,039 A * | 2/1982 | Kawai | .................. | C08K 5/1575 524/570 |
| 4,739,102 A * | 4/1988 | Tokunaga | ............. | C07C 69/732 560/75 |
| 4,954,291 A * | 9/1990 | Kobayashi | ........... | C08K 5/0008 252/1 |
| 5,198,484 A | 3/1993 | Mannion | | |
| 6,245,843 B1 | 6/2001 | Kobayashi et al. | | |
| 6,417,254 B1 | 7/2002 | Kobayashi | | |
| 6,673,856 B1 | 1/2004 | Mentink | | |
| 9,206,138 B2 * | 12/2015 | Maeda | .................. | C07D 233/60 |
| 10,138,275 B2 * | 11/2018 | Liu | ........................ | A61K 38/12 |
| 10,894,874 B2 * | 1/2021 | Iwasaki | ................ | C08K 5/0083 |
| 2002/0028864 A1 | 3/2002 | Kobayashi et al. | | |
| 2003/0077327 A1* | 4/2003 | Durig | ..................... | A61P 29/00 424/495 |
| 2003/0109610 A1 | 6/2003 | Nomoto et al. | | |
| 2005/0171230 A1 | 8/2005 | Ishikawa et al. | | |

(Continued)

FOREIGN PATENT DOCUMENTS

| | | |
|---|---|---|
| CN | 1241190 A | 1/2000 |
| CN | 1246881 A | 3/2000 |

(Continued)

OTHER PUBLICATIONS

Office Action issued in corresponding Chinese Application No. 201780047038.6, dated Sep. 14, 2020 (11 pages).
International Search Report issued in International Application No. PCT/JP2017/026379; dated Oct. 24, 2017 (4 pages).
Written Opinion of the International Searching Authority issued in International Application No. PCT/JP2017/026379; dated Oct. 24, 2017 (9 pages).
Database WPI Week201641, Thompson Scientific, london, GB; XP-002797357 (2 pages).
Extended European Search Report issued in European Application No. 17834169.9 , dated Feb. 14, 2020 (9 pages).

(Continued)

*Primary Examiner* — Tae H Yoon
(74) *Attorney, Agent, or Firm* — Osha Bergman Watanabe & Burton LLP

(57) ABSTRACT

The present invention aims to provide a method for improving the fluidity of a crystal nucleating agent for polyolefin resins without impairing other properties, and a polyolefin resin composition containing the crystal nucleating agent with improved fluidity and having excellent properties including transparency, and a molded article thereof. Adjustment to specific characteristics can improve the fluidity of a crystal nucleating agent for polyolefin resins, and the use of such a crystal nucleating agent having specific characteristics remarkably improves the workability during molding processing and provides a polyolefin resin composition excellent in properties such as transparency, and a molded article thereof.

7 Claims, No Drawings

(56) References Cited

U.S. PATENT DOCUMENTS

| | | |
|---|---|---|
| 2006/0173108 A1 | 8/2006 | Xu et al. |
| 2010/0040813 A1 | 2/2010 | Wada et al. |
| 2011/0105657 A1 | 5/2011 | Tanji et al. |
| 2012/0048146 A1* | 3/2012 | Wyart .................. C07H 15/18 106/505 |
| 2012/0296018 A1 | 11/2012 | Haruna et al. |
| 2016/0115295 A1 | 4/2016 | Yamazaki et al. |
| 2020/0131331 A1 | 4/2020 | Zhao et al. |

FOREIGN PATENT DOCUMENTS

| | | |
|---|---|---|
| CN | 1649951 A | 8/2005 |
| CN | 101111551 A | 1/2008 |
| CN | 101511930 A | 8/2009 |
| CN | 103497484 A | 1/2014 |
| CN | 104910616 A | 9/2015 |
| CN | 106715556 A | 5/2017 |
| EP | 1209190 A1 | 5/2002 |
| EP | 1375583 A1 | 1/2004 |
| JP | S51122150 A | 10/1976 |
| JP | S5721440 A | 2/1982 |
| JP | S5947705 B2 | 11/1984 |
| JP | S60101131 A | 6/1985 |
| JP | H06-145431 A | 5/1994 |
| JP | H07032454 A | 2/1995 |
| JP | H07118512 A | 5/1995 |
| JP | H08-245843 A | 9/1996 |
| JP | 2001081236 A | 3/2001 |
| JP | 2001-240698 A | 9/2001 |
| JP | 2002060602 A | 2/2002 |
| JP | 2002332359 A | 11/2002 |
| JP | 2002356586 A | 12/2002 |
| JP | 2003096246 A | 4/2003 |
| JP | 2007-297465 A | 11/2007 |
| JP | 2009507982 A | 2/2009 |
| JP | 2010275535 A | 12/2010 |
| JP | 2011207991 A | 10/2011 |
| JP | 2012233149 A | 11/2012 |
| JP | 2013209662 A | 10/2013 |
| JP | 2015030849 A | 2/2015 |
| JP | 5920524 B2 | 5/2016 |
| JP | 2016121303 A | 7/2016 |
| WO | 9833851 A1 | 8/1998 |
| WO | 9918108 A1 | 4/1999 |
| WO | 2002077094 A1 | 10/2002 |
| WO | 2006083640 A1 | 8/2006 |
| WO | 2007032797 A1 | 3/2007 |
| WO | 2009139350 A1 | 11/2009 |
| WO | 2011122264 A1 | 10/2011 |
| WO | 2014136824 A1 | 9/2014 |
| WO | 2014192812 A1 | 12/2014 |
| WO | 2015180680 A1 | 12/2015 |
| WO | WO 2015/180680 A1 * | 12/2015 |
| WO | 2016/088767 A1 | 6/2016 |

OTHER PUBLICATIONS

Office Action issued in Chinese Application No. 201780047038.6, dated May 24, 2021 (15 pages).

Notice of Reasons for Revocation issued in Japanese Application No. 2016-149528, dated Mar. 4, 2021 (26 pages).

Office Action issued in counterpart Chinese Application No. 201780055021.5; dated Jan. 24, 2022 (10 pages).

International Search Report issued in International Application No. PCT/JP2017/028740; dated Oct. 31, 2017 (1 page).

Written Opinion of the International Searching Authority issued in International Application No. PCT/JP2017/028740; dated Oct. 31, 2017 (3 pages).

Extended European Search Report issued in European Application No. 17850911.3, dated Apr. 8, 2020 (11 pages).

Office Action issued in corresponding Japanese Application No. 2016181073; dated Dec. 24, 2019 (15 pages).

Office Action issued in U.S. Appl. No. 16/333,387, dated Oct. 13, 2020 (29 pages).

Ma, C. et al.,"Research Advance on Nucleating Agents of PP," Modern Plastics Processing and Applications, pp. 41-44, Feb. 2002 (4 pages) with English Abstract.

Li, C. et al., "Morphology, Crystallization Behavior and Tensile Properties of ß-Nucleated Isotactic Polypropylene Fibrous Membranes Prepared by Melt Electrospinning," Chinese Journal of Polymer Science, vol. 32, No. 9, pp. 1167-1175, Apr. 21, 2014 (9 pages).

International Search Report issued in International Application No. PCT/JP2017/033009; dated Oct. 31, 2017 (2 pages).

Written Opinion issued in International Application No. PCT/JP2017/033009; dated Oct. 31, 2017 (3 pages).

Office Action issued in U.S. Appl. No. 16/333,387, dated Aug. 1, 2022 (23 pages).

* cited by examiner

CRYSTAL NUCLEATING AGENT FOR POLYOLEFIN RESIN, METHOD FOR PRODUCING CRYSTAL NUCLEATING AGENT FOR POLYOLEFIN RESIN, AND METHOD FOR IMPROVING FLUIDITY OF CRYSTAL NUCLEATING AGENT FOR POLYOLEFIN RESIN

CROSS-REFERENCE TO RELATED APPLICATIONS

The present application is a U.S. national phase entry under 35 U.S.C. § 371 of International Application No. PCT/JP2017/026379, filed on Jul. 21, 2017, which claims priority to Japanese applications No. 2016-149528, filed on Jul. 29, 2016, and 2017-128572, filed on Jun. 30, 2017, the entire content of each of these applications is explicitly incorporated herein by reference.

TECHNICAL FIELD

The present invention relates to improvement of the fluidity of a crystal nucleating agent for polyolefin resins. Specifically, the present invention relates to a method for improving the fluidity, a method for producing a crystal nucleating agent for polyolefin resins with improved fluidity including the above method, a crystal nucleating agent for polyolefin resins with improved fluidity obtained by the method, and a polyolefin resin composition and a molded article thereof each prepared using the crystal nucleating agent.

BACKGROUND ART

Polyolefin resins such as polyethylene or polypropylene are inexpensive and have well-balanced properties, and therefore are used for various applications as general-purpose plastics. Polyolefin resins are commonly crystalline and are often used together with a crystal nucleating agent with an aim of improving the production efficiency or with an aim of improving the mechanical properties, thermal properties, and optical properties. In particular, the use of a crystal nucleating agent is essential for improvement of the transparency that is an optical property.

The crystal nucleating agent is classified as an inorganic crystal nucleating agent (e.g., talc) or an organic crystal nucleating agent (e.g., a diacetal compound, a metal salt of a carboxylic acid or a phosphoric acid ester). The organic crystal nucleating agent is further classified as a soluble crystal nucleating agent or an insoluble crystal nucleating agent. For improvement of the optical properties such as transparency, a soluble organic crystal nucleating agent typified by the diacetal compound is particularly effective and is often used.

A feature of general-purpose plastics, in particular, polyolefin resins, is inexpensiveness. For achieving this feature, excellent productivity is important, and various measures have been devised such as shortening of the molding cycle by addition of a crystal nucleating agent as described above. The feeding property of the raw material is also an important factor, and each raw material needs to have an excellent feed property, i.e., excellent fluidity. However, the crystal nucleating agent, in particular a diacetal crystal nucleating agent, has poor fluidity to be disadvantageous in terms of productivity.

Various efforts therefore have been made on improvement of the fluidity of a crystal nucleating agent including diacetal compounds. For example, methods for improving the fluidity by granulation (Patent Literatures 1 to 3), methods for improving the fluidity not by granulation but by adding a fluidity improver (Patent Literatures 4 to 7), and like methods have been proposed, and these methods are used in practice.

Recently, general-purpose plastics are desired to have further improved productivity, and the feeding property, i.e., fluidity, of the raw material has been desired to be further improved. Further improvement of the fluidity of the crystal nucleating agent, in particular a diacetal crystal nucleating agent, has been a difficult issue for improvement of the productivity.

As mentioned above, the following two methods are commonly known and widely employed as the method for improving the fluidity (not limited to the fluidity of a crystal nucleating agent).
(1) Method for controlling the particle shape such as particle size
(2) Method for adding an additive effective for improvement of the fluidity, i.e., a fluidity improver As described above, recent requirements for fluidity are getting stricter and the method (2) hardly satisfies the requirements. Therefore, the method (1) is more likely to be employed for applications which have more strict requirements for the fluidity.

In the case of the method (1), the fluidity is commonly improved along with an increase in the particle size. A method for granulating a nucleating agent alone or a mixture containing a nucleating agent and other additive(s), a method of mixing a nucleating agent with a resin in advance to prepare a masterbatch, or the like method is employed as a general method for increasing the particle size.

However, in the case where the particle size is increased by granulation or the like, the fluidity is improved but the dispersibility or solubility of the nucleating agent in polyolefin resins tends to be lowered. As a result, not only a problem of lowering the original performance of the nucleating agent, such as transparency, but also a problem in relation to the appearance such as white spots may arise. Accordingly, in the field which has a particularly strict requirement for the dispersibility, a method of adding additives such as a binder for granulation is commonly employed.

As the binder, various compounds have been considered. Organic acid monoglyceride that is widely used as an additive for polyolefins, such as an antistatic agent or a lubricant, is known as a highly usable binder.

The granulation method is also important in relation to the fluidity, and the method has been studied in various ways.

As a recent trend, in overall consideration of the environmental problems or the like, or with an aim of ensuring the flexibility of the compounding formulation, the amount of a component other than the crystal nucleating agent is being reduced as far as possible. Now, a method for controlling the particle size without adding a binder or a method for performing granulation with no binder or with only a slight amount of a binder is desired. In some applications, an influence of a binder on the performance of the nucleating agent itself is concerned. From this standpoint too, reduction of the binder amount is desired. In particular, this trend is significant in medical applications, and development of a method for improving the fluidity without using an additive that is a heterologous component is strongly desired. A method for performing granulation without using an undesired heterologous component by exclusively adding an antioxidant, an antacid, and a lubricant has been proposed (Patent Literature 8). However, when the amount of the binder is less than a certain amount, granulation is difficult, and therefore, there is a limit on reduction of the binder amount.

Moreover, in some applications, a requirement in relation to the dispersibility or solubility in a resin described above becomes stricter. In conventional granulation methods, a large amount of binder having a relatively low melting point, such as an organic acid monoglyceride, needs to be added. In such a case, however, another problem such as caking caused by the binder arises and the problem needs to be addressed.

In particular, in the case of a crystal nucleating agent such as a diacetal compound, there is a problem in relation to the secondary aggregation properties or the like. In addition, the dispersibility or solubility in a melted resin is known to markedly influence the nucleating agent performance. It is difficult to satisfy all the requirements sufficiently by granulation in a conventionally known system, and improvement of the state of the art is strongly desired.

CITATION LIST

Patent Literature

Patent Literature 1: WO 98/33851
Patent Literature 2: JP 2001-81236 A
Patent Literature 3: WO 2002/077094
Patent Literature 4: JP 2009-507982 T
Patent Literature 5: JP 2013-209662 A
Patent Literature 6: JP 2015-30849 A
Patent Literature 7: WO 2014/136824
Patent Literature 8: JP 2002-332359 A

SUMMARY OF INVENTION

Technical Problem

The present invention aims to provide a method for improving the fluidity of a crystal nucleating agent for polyolefin resins without essentially using an additive, a method for producing a crystal nucleating agent for polyolefin resins with improved fluidity including the above method, a crystal nucleating agent for polyolefin resins with improved fluidity obtained by the method, and a polyolefin resin composition and a molded article thereof each including the crystal nucleating agent.

Solution to Problem

The present invention provides a method for improving the fluidity of a crystal nucleating agent for polyolefin resins, a method for producing a crystal nucleating agent for polyolefin resins with improved fluidity including the above method, a crystal nucleating agent for polyolefin resins with improved fluidity obtained by the method, and a polyolefin resin composition and a molded article thereof each containing the crystal nucleating agent.

The present invention relates to a crystal nucleating agent for polyolefin resins having an aerated bulk density within a range of 0.25 to 0.50 g/cm$^3$ and a packed bulk density within a range of 0.35 to 0.80 g/cm$^3$.

The crystal nucleating agent for polyolefin resins preferably has an angle of repose of 48 degrees or smaller.

The crystal nucleating agent for polyolefin resins is preferably a diacetal compound represented by the following formula (1):

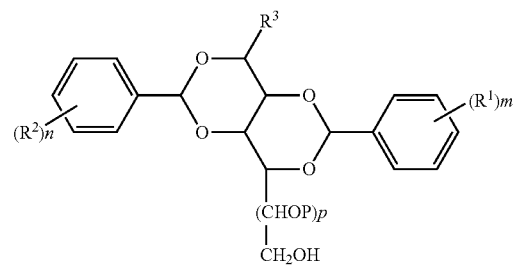

wherein $R^1$ and $R^2$ are the same as or different from each other and each represent a hydrogen atom, a C1-C4 linear or branched alkyl group, a C1-C4 linear or branched alkoxy group, a C1-C4 linear or branched alkoxy carbonyl group, or a halogen atom; $R^3$ represents a hydrogen atom, a C1-C4 linear or branched alkyl group, a C2-C4 linear or branched alkenyl group, or a C1-C4 linear or branched hydroxy alkyl group; m and n each represent an integer of 1 to 5; p represents 0 or 1; and two $R^2$s optionally bind to each other to form a tetralin ring together with a benzene ring to which they are bonded and two Res optionally bind to each other to form a tetralin ring together with a benzene ring to which they are bonded.

In the formula (1), preferably, $R^1$ and $R^2$ are the same as or different from each other and each represent a methyl group or an ethyl group, $R^3$ represents a hydrogen atom, m and n each represent an integer of 1 or 2, and p represents 1.

In the formula (1), preferably, $R^1$ and $R^2$ are the same as or different from each other and each represent a propyl group or a propoxy group, $R^3$ represents a propyl group or a propenyl group, m and n each represent 1, and p represents 1.

The crystal nucleating agent for polyolefin resins is preferably a granule obtained by preparing a mixture containing a starting powder of the crystal nucleating agent for polyolefin resins and a compound having a binder effect, extrusion-granulating the mixture, and removing the compound having a binder effect from the extrusion-granulation product.

The crystal nucleating agent for polyolefin resins preferably has a powdering rate of 40% or lower.

The granule preferably has a cylindrical shape with a diameter within a range of 0.5 to 5.0 mm.

The crystal nucleating agent for polyolefin resins is preferably a compression product obtained by dry compression.

The dry compression is preferably carried out by a roller compression method.

The dry compression is preferably carried out with a roll pressure within a range of 0.1 to 10 MPa.

In a sieve analysis performed on the crystal nucleating agent for polyolefin resins without pulverizing a secondary aggregate under the condition in conformity with JIS K 0069 (1992), the proportion of a residue left on a JIS test sieve with an aperture of 1 mm relative to the total weight of the tested crystal nucleating agent is preferably 25% by weight or less.

In laser diffraction particle size distribution measurement performed on the crystal nucleating agent for polyolefin resins, the proportion of a coarse particle having a particle size of 15 μm or larger relative to the total volume of the measured crystal nucleating agent is preferably 50% by volume or more.

The present invention also relates to a method for producing a crystal nucleating agent for polyolefin resins with improved fluidity, including: (i) mixing a starting powder of a crystal nucleating agent for polyolefin resins and a compound having a binder effect; (ii) granulating the mixture obtained in the step (i) by extrusion granulation; and (iii) removing the compound having a binder effect mixed in the step (i) from the granulation product obtained in the step (ii).

The crystal nucleating agent for polyolefin resins obtained in the step (iii) preferably has an aerated bulk density of 0.25 to 0.50 g/cm$^3$, a packed bulk density within a range of 0.30 to 0.80 g/cm$^3$, and a powdering rate of 40% or lower.

The present invention further relates to a method for producing a crystal nucleating agent for polyolefin resins, including a dry compression step by a roller compression method.

The compression step is preferably carried out with a roll pressure within a range of 0.1 to 10 MPa.

The present invention further relates to a polyolefin resin composition including: a polyolefin resin; and the crystal nucleating agent for polyolefin resins or a crystal nucleating agent for polyolefin resins produced by the method for producing a crystal nucleating agent for polyolefin resins.

The present invention further relates to a polyolefin resin molded article produced using the polyolefin resin composition as a raw material.

The present invention further relates to a method for improving the fluidity of a crystal nucleating agent for polyolefin resins, including adjusting the nucleating agent to have an aerated bulk density within a range of 0.25 to 0.50 g/cm$^3$, a packed bulk density within a range of 0.3 to 0.80 g/cm$^3$, and a powdering rate of 40% or lower.

The present invention still further relates to a method for improving the fluidity of a crystal nucleating agent for polyolefin resins, including a dry compression step by a roller compression method.

Advantageous Effects of Invention

The crystal nucleating agent for polyolefin resins of the present invention has very excellent fluidity to remarkably contribute to the improvement of the productivity or the like. In relation to the dispersibility or solubility in polyolefin resins which has been a problem, the crystal nucleating agent for polyolefin resins of the present invention shows similar or higher dispersibility or solubility in polyolefin resins compared to conventional crystal nucleating agents, which is at a practically usable level. Thus, it can sufficiently show its performance as a crystal nucleating agent. Also, it can provide a polyolefin resin molded article with properties or an appearance each at a desired level. The crystal nucleating agent for polyolefin resins of the present invention therefore can be reliably used. Consequently, the crystal nucleating agent for polyolefin resins of the present invention is widely usable in various applications and can provide a molded article with excellent properties, being useful in many applications.

DESCRIPTION OF EMBODIMENTS

<Crystal Nucleating Agent for Polyolefin Resins>

The crystal nucleating agent for polyolefin resins of the present invention (hereafter, also simply referred to as a "crystal nucleating agent") has an aerated bulk density within a range of 0.25 to 0.50 g/cm$^3$ and a packed bulk density within a range of 0.30 to 0.80 g/cm$^3$. The aerated bulk density is preferably within a range of 0.30 to 0.45 g/cm$^3$, more preferably within a range of 0.35 to 0.45 g/cm$^3$. The packed bulk density is preferably within a range of 0.35 to 0.75 g/cm$^3$, more preferably within a range of 0.35 to 0.70 g/cm$^3$. Commonly, when the bulk density is higher, the fluidity tends to be more excellent. In the present invention, the bulk density is markedly increased compared to that of conventional products, which presumably contributes to the improvement of the fluidity. The packed bulk density is a value obtained by densifying the sample that has been subjected to the measurement of the aerated bulk density by tapping or the like and measuring the bulk density of the sample. The packed bulk density is normally larger than the aerated bulk density.

Here, the bulk density refers to the density of a material filled in a container, calculated using the interior capacity of the container as the volume of the material. The bulk density obtained by the measurement performed on a material slowly (without pressurization) filled in the container to a roughly packed state is the aerated bulk density, and the bulk density obtained by the measurement performed on the material further tapped under a certain condition to a densely packed state is the packed bulk density. In the case of a granulation product, for example, the granulation product with a larger bulk density is commonly considered to have fewer voids therein to be tightly compacted. In the case where the bulk density is markedly increased after granulation when the bulk densities before and after the granulation are compared, production of a favorable granulation product in which voids among particles present before the granulation are decreased can be confirmed.

The bulk density is a value easily obtainable by measuring the capacity of the container and the weight of the contents filled therein as described above, and it can be measured, for example, by the following method.

A funnel is set on the opening of a measuring cylinder vertically, and a predetermined amount of a sample is slowly (without pressurization) filled into the measuring cylinder thorough the funnel, and the weight of the sample in the measuring cylinder is measured using a scale. The aerated bulk density is obtained by the following equation (1) using the obtained weight. Subsequently, the measuring cylinder is dropped onto a rubber sheet or the like from a certain height (tapping) for a predetermined times, and the volume of the sample in the measuring cylinder is read. The packed bulk density is obtained by the following equation (2).

Aerated bulk density (g/cm$^3$)=Weight of sample (g)/ Capacity of measuring cylinder (cm$^3$)   Equation (1):

Packed bulk density (g/cm$^3$)=Weight of sample (g)/ Volume of sample after tapping (cm$^3$)   Equation (2):

In the present invention, the bulk density of the obtained crystal nucleating agent is recommended to be set within a certain range also from the standpoint of the dispersibility or solubility in resin. The crystal nucleating agent with too large a bulk density is too much tightly compacted and therefore is likely to be less dispersed in resin, resulting in lower solubility. Accordingly, for favorable fluidity and excellent dispersibility or solubility in resin, it is important to set the bulk density within a certain range.

From the standpoint of improving the fluidity which is the aim of the present invention, the crystal nucleating agent of the present invention has an angle of repose of preferably 48 degrees or smaller, more preferably 46 degrees or smaller, still more preferably 45 degrees or smaller, particularly preferably 40 degrees or smaller. With the angle of repose of larger than 48 degrees, sufficient fluidity is less likely to be achieved.

Examples of the crystal nucleating agent of the present invention include diacetal compounds, carboxylate compounds, phosphate compounds, amide compounds, and rosin compounds. In particular, when the crystal nucleating agent of the present invention is a diacetal compound, the effect of the present invention is most significant. Here, the type of the diacetal compound is not particularly limited as long as the effect of the present invention is exerted.

The diacetal compound is not particularly limited, and a favorable example thereof is a diacetal compound represented by the following formula (1):

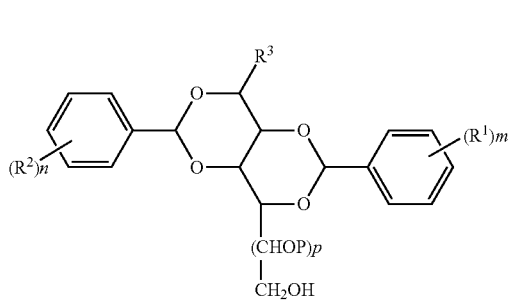

wherein $R^1$ and $R^2$ are the same as or different from each other and each represent a hydrogen atom, a C1-C4 linear or branched alkyl group, a C1-C4 linear or branched alkoxy group, a C1-C4 linear or branched alkoxy carbonyl group, or a halogen atom; $R^3$ represents a hydrogen atom, a C1-C4 linear or branched alkyl group, a C2-C4 linear or branched alkenyl group, or a C1-C4 linear or branched hydroxy alkyl group; m and n each represent an integer of 1 to 5; p represents 0 or 1; and two $R^2$s optionally bind to each other to form a tetralin ring together with a benzene ring to which they are bonded and two Res optionally bind to each other to form a tetralin ring together with a benzene ring to which they are bonded.

Among the diacetal compounds, more preferred are compounds represented by the formula (1) wherein $R^1$ and $R^2$ are the same as or different from each other and each represent a methyl group or an ethyl group, $R^3$ represents a hydrogen atom, m and n each represent an integer of 1 or 2, and p represents 1 and compounds represented by the formula (1) wherein $R^1$ and $R^2$ each represent a propyl group or a propoxy group, $R^3$ represents a propyl group or a propenyl group, m and n each represent 1, and p represents 1.

In addition, examples of more preferred compounds include the following compounds: compounds represented by the formula (1) wherein $R^1$ and $R^2$ each represent a propyl group or a propoxy group, $R^3$ represents a propyl group or a propenyl group, m and n each represents 1, and p represents 1.

As specific embodiments of the diacetal compounds, the following compounds can be exemplified: 1,3:2,4-di-O-benzylidene-D-sorbitol, 1,3:2,4-bis-O-(methylbenzylidene)-D-sorbitol, 1,3:2,4-bis-O-(o-methylbenzylidene)-D-sorbitol, 1,3:2,4-bis-O-(m-methylbenzylidene)-D-sorbitol, 1,3:2,4-bis-O-(p-methylbenzylidene)-D-sorbitol, 1,3:2,4-bis-O-(ethylbenzylidene)-D-sorbitol, 1,3:2,4-bis-O-(o-ethylbenzylidene)-D-sorbitol, 1,3:2,4-bis-O-(m-ethylbenzylidene)-D-sorbitol, 1,3:2,4-bis-O-(p-ethylbenzylidene)-D-sorbitol, 1,3:2,4-bis-O-(o-isopropylbenzylidene)-D-sorbitol, 1,3:2,4-bis-O-(m-isopropylbenzylidene)-D-sorbitol, 1,3:2,4-bis-O-(p-isopropylbenzylidene)-D-sorbitol, 1,3:2,4-bis-O-(o-n-propylbenzylidene)-D-sorbitol, 1,3:2,4-bis-O-(m-n-propylbenzylidene)-D-sorbitol, 1,3:2,4-bis-O-(p-n-propylbenzylidene)-D-sorbitol, 1,3:2,4-bis-O-(o-n-butylbenzylidene)-D-sorbitol, 1,3:2,4-bis-O-(m-n-butylbenzylidene)-D-sorbitol, 1,3:2,4-bis-O-(p-n-butylbenzylidene)-D-sorbitol, 1,3:2,4-bis-O-(o-t-butylbenzylidene)-D-sorbitol, 1,3:2,4-bis-O-(m-t-butylbenzylidene)-D-sorbitol, 1,3:2,4-bis-O-(p-t-butylbenzylidene)-D-sorbitol, 1,3:2,4-bis-O-(dimethylbenzylidene)-D-sorbitol, 1,3:2,4-bis-O-(2',3'-dimethylbenzylidene)-D-sorbitol, 1,3:2,4-bis-O-(2',4'-dimethylbenzylidene)-D-sorbitol, 1,3:2,4-bis-O-(2',5'-dimethylbenzylidene)-D-sorbitol, 1,3:2,4-bis-O-(2',6'-dimethylbenzylidene)-D-sorbitol, 1,3:2,4-bis-O-(3',4'-dimethylbenzylidene)-D-sorbitol, 1,3:2,4-bis-O-(3',5'-dimethylbenzylidene)-D-sorbitol, 1,3:2,4-bis-O-(2',3'-diethylbenzylidene)-D-sorbitol, 1,3:2,4-bis-O-(2',4'-diethylbenzylidene)-D-sorbitol, 1,3:2,4-bis-O-(2',5'-diethylbenzylidene)-D-sorbitol, 1,3:2,4-bis-O-(2',6'-diethylbenzylidene)-D-sorbitol, 1,3:2,4-bis-O-(3',4'-diethylbenzylidene)-D-sorbitol, 1,3:2,4-bis-O-(3',5'-diethylbenzylidene)-D-sorbitol, 1,3:2,4-bis-O-(2',4',5'-trimethylbenzylidene)-D-sorbitol, 1,3:2,4-bis-O-(3',4',5'-trimethylbenzylidene)-D-sorbitol, 1,3:2,4-bis-O-(2',4',5'-triethylbenzylidene)-D-sorbitol, 1,3:2,4-bis-O-(3',4',5'-triethylbenzylidene)-D-sorbitol, 1,3:2,4-bis-O-(o-methoxybenzylidene)-D-sorbitol, 1,3:2,4-bis-O-(m-methoxybenzylidene)-D-sorbitol, 1,3:2,4-bis-O-(p-methoxybenzylidene)-D-sorbitol, 1,3:2,4-bis-O-(o-ethoxybenzylidene)-D-sorbitol, 1,3:2,4-bis-O-(m-ethoxybenzylidene)-D-sorbitol, 1,3:2,4-bis-O-(p-ethoxybenzylidene)-D-sorbitol, 1,3:2,4-bis-O-(o-isopropoxybenzylidene)-D-sorbitol, 1,3:2,4-bis-O-(m-isopropoxybenzylidene)-D-sorbitol, 1,3:2,4-bis-O-(p-isopropoxybenzylidene)-D-sorbitol, 1,3:2,4-bis-O-(o-n-propoxybenzylidene)-D-sorbitol, 1,3:2,4-bis-O-(m-n-propoxybenzylidene)-D-sorbitol, 1,3:2,4-bis-O-(p-n-propoxybenzylidene)-D-sorbitol, 1,3:2,4-bis-O-(o-methoxycarbonylbenzylidene)-D-sorbitol, 1,3:2,4-bis-o-(m-methoxycarbonylbenzylidene)-D-sorbitol, 1,3:2,4-bis-o-(p-methoxycarbonylbenzylidene)-D-sorbitol, 1,3:2,4-bis-O-(o-ethoxycarbonylbenzylidene)-D-sorbitol, 1,3:2,4-bis-O-(m-ethoxycarbonylbenzylidene)-D-sorbitol, 1,3:2,4-bis-O-(p-ethoxycarbonylbenzylidene)-D-sorbitol, 1,3:2,4-bis-O-(o-isopropoxycarbonylbenzylidene)-D-sorbitol, 1,3:2,4-bis-O-(m-isopropoxycarbonylbenzylidene)-D-sorbitol, 1,3:2,4-bis-O-(p-isopropoxycarbonylbenzylidene)-D-sorbitol, 1,3:2,4-bis-O-(o-n-propoxycarbonylbenzylidene)-D-sorbitol, 1,3:2,4-bis-O-(m-n-propoxycarbonylbenzylidene)-D-sorbitol, 1,3:2,4-bis-O-(p-n-propoxycarbonylbenzylidene)-D-sorbitol, 1,3:2,4-bis-O-(o-fluorobenzylidene)-D-sorbitol, 1,3:2,4-bis-O-(m-fluorobenzylidene)-D-sorbitol, 1,3:2,4-bis-O-(p-fluorobenzylidene)-D-sorbitol, 1,3:2,4-bis-O-(o-chlorobenzylidene)-D-sorbitol, 1,3:2,4-bis-O-(m-chlorobenzylidene)-D-sorbitol, 1,3:2,4-bis-O-(p-chlorobenzylidene)-D-sorbitol, 1,3:2,4-bis-O-(o-bromobenzylidene)-D-sorbitol, 1,3:2,4-bis-O-(m-bromobenzylidene)-D-sorbitol, 1,3:2,4-bis-O-(p-bromobenzylidene)-D-sorbitol, 1,3-O-benzylidene-2,4-O-(p-methylbenzylidene)-D-sorbitol, 1,3-O-(p-methylbenzylidene)-2,4-O-benzylidene-D-sorbitol, 1,3-O-benzylidene-2,4-O-(p-ethylbenzylidene)-D-sorbitol, 1,3-O-(p-ethylbenzylidene)-2,4-O-benzylidene-D-sorbitol, 1,3-O-benzylidene-2,4-O-(p-chlorobenzylidene)-D-sorbitol, 1,3-O-(p-chlorobenzylidene)-2,4-O-benzylidene-D-sorbitol, 1,3-O-benzylidene-2,4-O-(2',4'-dimethylbenzylidene)-D-sorbitol, 1,3-O-(2',4'-dimethylbenzylidene)-2,4-O-benzylidene-D-sorbitol, 1,3-O-benzylidene-2,4-O-(3',4'-dimethylbenzylidene)-D-sorbitol, 1,3-O-(3',4'-dimethylbenzylidene)-2,4-O-benzylidene-D-sorbitol, 1,3-O-(p-methylbenzylidene)-2,4-O-(p-ethylbenzylidene)-D-sorbitol, 1,3-O-(p-ethylbenzylidene)-2,4-O-(p-methylbenzylidene)-D-sorbitol, 1,3-O-(p-methylbenzylidene)-2,4-O-(3',4'-dimethylbenzylidene)-D-sorbitol, 1,3-O-(3',4'-dimethylbenzylidene)-2,4-O-p-methylbenzylidene-D-sorbitol, 1,3-O-(p-ethylbenzylidene)-2,4-O-(3',4'-dimethylbenzylidene)-D-sorbitol, 1,3-O-(3',4'-dimethylbenzylidene)-2,4-O-p-ethylbenzylidene-D-sorbitol, 1,3-O-(p-methylbenzylidene)-2,4-O-(p-chlorobenzylidene)-D-sorbitol, 1,3-O-(p-chlorobenzylidene)-2,4-O-(p-methylbenzylidene)-D-sorbitol, 1,3:2,4-bis-O-(3',4'-dichlorobenzylidene)-D-sorbitol, 1,3:2,4-bis-O-benzylidene-1-methylsorbitol, 1,3:2,4-bis-O-(p-methylbenzylidene)-1-methylsorbitol, 1,3:2,4-bis-O-(p-ethylbenzylidene)-1-methylsorbitol, 1,3:2,4-bis-O-(p-n-propylbenzylidene)-1-methylsorbitol, 1,3:2,4-bis-O-(2',3'-dimethylbenzylidene)-1-methylsorbitol, 1,3:2,4-bis-O-(2',4'-dimethylbenzylidene)-1-methylsorbitol, 1,3:2,4-bis-O-(2',5'-dimethylbenzylidene)-1-methylsorbitol, 1,3:2,4-bis-O-(2',6'-dimethylbenzylidene)-1-methylsorbitol, 1,3:2,4-bis-O-(3',4'-dimethylbenzylidene)-1-methylsorbitol, 1,3:2,4-bis-O-(3',5'-dimethylbenzylidene)-1-methylsorbitol, 1,3:2,4-bis-O-(2',3'-diethylbenzylidene)-1-methylsorbitol, 1,3:2,4-bis-O-(2',4'-diethylbenzylidene)-1-methylsorbitol, 1,3:2,4-bis-O-(2',5'-diethylbenzylidene)-1-methylsorbitol, 1,3:2,4-bis-O-(2',6'-diethylbenzylidene)-1-methylsorbitol, 1,3:2,4-bis-O-(3',4'-diethylbenzylidene)-1-methylsorbitol, 1,3:2,4-bis-O-(3',5'-diethylbenzylidene)-1-methylsorbitol, 1,3:2,4-bis-O-(3'-methyl-4'-methoxybenzylidene)-1-methylsorbitol, 1,3:2,4-bis-O-(3',4'-dichlorobenzylidene)-1-methylsorbitol, 1,3:2,4-bis-O-(p-methoxycarbonylbenzylidene)-1-methylsorbitol, 1,3:2,4-bis-O-(3'-methyl-4'-fluorobenzylidene)-1-methylsorbitol, 1,3:2,4-bis-O-(3'-bromo-4'-ethylbenzylidene)-1-methylsorbitol, 1,3:2,4-bis-O-benzylidene-1-ethylsorbitol, 1,3:2,4-bis-O-(p-methylbenzylidene)-1-ethylsorbitol, 1,3:2,4-bis-O-(p-ethylbenzylidene)-1-ethylsorbitol, 1,3:2,4-bis-O-(p-n-propylbenzylidene)-1-ethylsorbitol, 1,3:2,4-bis-O-(2',3'-dimethylbenzylidene)-1-ethylsorbitol, 1,3:2,4-bis-O-(2',4'-dimethylbenzylidene)-1-ethylsorbitol, 1,3:2,4-bis-O-(2',5'-dimethylbenzylidene)-1-ethylsorbitol, 1,3:2,4-bis-O-(2',6'-dimethylbenzylidene)-1-ethylsorbitol, 1,3:2,4-bis-O-(3',4'-dimethylbenzylidene)-1-ethylsorbitol, 1,3:2,4-bis-O-(3',5'-dimethylbenzylidene)-1-ethylsorbitol, 1,3:2,4-bis-O-(2',3'-diethylbenzylidene)-1-ethylsorbitol, 1,3:2,4-bis-O-(2',4'-diethylbenzylidene)-1-ethylsorbitol, 1,3:2,4-bis-O-(2',5'-diethylbenzylidene)-1-ethylsorbitol, 1,3:2,4-bis-O-(2',6'-diethylbenzylidene)-1-ethylsorbitol, 1,3:2,4-bis-O-(3',4'-diethylbenzylidene)-1-ethylsorbitol, 1,3:2,4-bis-O-(3',5'-diethylbenzylidene)-1-ethylsorbitol, 1,3:2,4-bis-O-(3'-methyl-4'-methoxybenzylidene)-1-ethylsorbitol, 1,3:2,4-bis-O-(3',4'-dichlorobenzylidene)-1-ethylsorbitol, 1,3:2,4-bis-O-(p-methoxycarbonylbenzylidene)-1-ethylsorbitol, 1,3:2,4-bis-O-(3'-methyl-4'-fluorobenzylidene)-1-ethylsorbitol, 1,3:2,4-bis-O-(3'-bromo-4'-ethylbenzylidene)-1-ethylsorbitol, 1,3:2,4-bis-O-benzylidene-1-n-propylsorbitol, 1,3:2,4-bis-O-(p-methylbenzylidene)-1-n-propylsorbitol, 1,3:2,4-bis-O-(p-ethylbenzylidene)-1-n-propylsorbitol, 1,3:2,4-bis-O-(p-n-propylbenzylidene)-1-n-propylsorbitol, 1,3:2,4-bis-O-(2',3'-dimethylbenzylidene)-1-n-propylsorbitol, 1,3:2,4-bis-O-(2',4'-dimethylbenzylidene)-1-n-propylsorbitol, 1,3:2,4-bis-O-(2',5'-dimethylbenzylidene)-1-n-propylsorbitol, 1,3:2,4-bis-O-(2',6'-dimethylbenzylidene)-1-n-propylsorbitol, 1,3:2,4-bis-O-(3',4'-dimethylbenzylidene)-1-n-propylsorbitol, 1,3:2,4-bis-O-(3',4'-dimethylbenzylidene)-1-n-propylsorbitol, 1,3:2,4-bis-O-(3',5'-dimethylbenzylidene)-1-n-propylsorbitol, 1,3:2,4-bis-O-(2',3'-diethylbenzylidene)-1-n-propylsorbitol, 1,3:2,4-bis-O-(2',4'-diethylbenzylidene)-1-n-propylsorbitol, 1,3:2,4-bis-O-(2',5'-diethylbenzylidene)-1-n-propylsorbitol, 1,3:2,4-bis-O-(2',6'-diethylbenzylidene)-1-n-propylsorbitol, 1,3:2,4-bis-O-(3',4'-diethylbenzylidene)-1-n-propylsorbitol, 1,3:2,4-bis-O-(3',5'-diethylbenzylidene)-1-n-propylsorbitol, 1,3:2,4-bis-O-(3'-methyl-4'-methoxybenzylidene)-1-n-propylsorbitol, 1,3:2,4-bis-O-(3',4'-dichlorobenzylidene)-1-n-propylsorbitol, 1,3:2,4-bis-O-(p-methoxycarbonylbenzylidene)-1-n-propylsorbitol, 1,3:2,4-bis-O-(p-ethoxycarbonylbenzylidene)-1-n-propylsorbitol, 1,3:2,4-bis-O-(p-propoxycarbonylbenzylidene)-1-n-propylsorbitol, 1,3-O-(p-n-propylbenzylidene)-2,4-O-(p-propoxybenzylidene)-1-n-propylsorbitol, 1,3-O-(p-propoxybenzylidene)-2,4-O-(p-n-propylbenzylidene)-1-n-propylsorbitol, 1,3:2,4-bis-O-(3'-methyl-4'-fluorobenzylidene)-1-n-propylsorbitol, 1,3:2,4-bis-O-(3'-bromo-4'-ethylbenzylidene)-1-n-propylsorbitol, 1,3:2,4-bis-O-(p-n-propylbenzylidene)-1-propenylsorbitol, 1,3:2,4-bis-O-(p-ethoxycarbonylbenzylidene)-1-propenylsorbitol, 1,3:2,4-bis-O-(p-propoxycarbonylbenzylidene)-1-propenylsorbitol, 1,3-O-(p-n-propylbenzylidene)-2,4-O-(p-propoxybenzylidene)-1-propenylsorbitol, 1,3-O-(p-propoxybenzylidene)-2,4-O-(p-n-propylbenzylidene)-1-propenylsorbitol, 1,3:2,4-bis-O-benzylidene-1-allylsorbitol, 1,3:2,4-bis-O-(p-methylbenzylidene)-1-allylsorbitol, 1,3:2,4-bis-O-(p-ethylbenzylidene)-1-allylsorbitol, 1,3:2,4-bis-O-(p-n-propylbenzylidene)-1-allylsorbitol, 1,3:2,4-bis-O-(2',3'-dimethylbenzylidene)-1-allylsorbitol, 1,3:2,4-bis-O-(2',4'-dimethylbenzylidene)-1-allylsorbitol, 1,3:2,4-bis-O-(2',5'-dimethylbenzylidene)-1-allylsorbitol, 1,3:2,4-bis-O-(2',6'-dimethylbenzylidene)-1-allylsorbitol, 1,3:2,4-bis-O-(3',4'-dimethylbenzylidene)-1-allylsorbitol, 1,3:2,4-bis-O-(3',5'-dimethylbenzylidene)-1-allylsorbitol, 1,3:2,4-bis-O-(2',3'-diethylbenzylidene)-1-allylsorbitol, 1,3:2,4-bis-O-(2',4'-diethylbenzylidene)-1-allylsorbitol, 1,3:2,4-bis-O-(2',5'-diethylbenzylidene)-1-allylsorbitol, 1,3:2,4-bis-O-(2',6'-diethylbenzylidene)-1-allylsorbitol, 1,3:2,4-bis-O-(3',4'-diethylbenzylidene)-1-allylsorbitol, 1,3:2,4-bis-O-(p-ethoxycarbonylbenzylidene)-1-allylsorbitol, 1,3:2,4-bis-O-(p-propoxycarbonylbenzylidene)-1-allylsorbitol, 1,3-O-(p-n-propylbenzylidene)-2,4-O-(p-propoxybenzylidene)-1-allylsorbitol, 1,3-O-(p-propoxybenzylidene)-2,4-O-(p-n-propylbenzylidene)-1-allylsorbitol, 1,3:2,4-bis-O-(3',5'-diethylbenzylidene)-1-n-propylsorbitol, 1,3:2,4-bis-O-(3'-methyl-4'-methoxybenzylidene)-1-allylsorbitol, 1,3:2,4-bis-O-(3',4'-dichlorobenzylidene)-1-allylsorbitol, 1,3:2,4-bis-O-(p-methoxycarbonylbenzylidene)-1-allylsorbitol, 1,3:2,4-bis-O-(3'-methyl-4'-fluorobenzylidene)-1-allylsorbitol, and 1,3:2,4-bis-O-(3'-bromo-4'-ethylbenzylidene)-1-allylsorbitol.

As particularly preferred embodiments, 1,3:2,4-bis-O-(p-methylbenzylidene)-D-sorbitol, 1,3:2,4-bis-O-(p-ethylbenzylidene)-D-sorbitol, 1,3:2,4-bis-O-(3',4'-dimethylbenzylidene)-D-sorbitol, and 1,3:2,4-bis-O-(p-n-propylbenzylidene)-1-propylsorbitol can be exemplified.

These diacetal compounds of the above specific embodiments may be used alone. In terms of other properties such as low-temperature processability, two or more types of diacetal compounds may be used in combination or in admixture.

In the case where diacetal compounds are used in combination or in admixture, examples of the combination thereof include a combination of 1,3:2,4-di-O-benzylidene-D-sorbitol and 1,3:2,4-bis-O-(p-methylbenzylidene)-D-sorbitol, a combination of 1,3:2,4-bis-O-(p-ethylbenzylidene)-

D-sorbitol and 1,3:2,4-bis-O-(3',4'-dimethylbenzylidene)-D-sorbitol, a combination of 1,3:2,4-dibenzylidene-D-sorbitol and 1,3:2,4-bis-O-(3',4'-dimethylbenzylidene)-D-sorbitol, a combination of 1,3:2,4-bis-O-(p-methylbenzylidene)-D-sorbitol and 1,3:2,4-bis-O-(3',4'-dimethylbenzylidene)-D-sorbitol, a combination of 1,3:2,4-bis-O-(p-chlorobenzylidene)-D-sorbitol and 1,3:2,4-bis-O(3',4'-dimethylbenzylidene)-D-sorbitol, and a combination of 1,3:2,4-bis-O-(3',4'-dichlorobenzylidene)-D-sorbitol and 1,3:2,4-bis-O-(3',4'-dimethylbenzylidene)-D-sorbitol.

The diacetal compounds can be easily produced by any of the production methods disclosed in, for example, JP S48-43748 B, JP S53-5165 A, JP S57-185287 A, JP H02-231488 A, and the like. Also, those presently commercially available as crystal nucleating agents for polyolefins, such as GELOL D, GELOL MD, and GELOL DXR available from New Japan Chemical Co., Ltd. and Millad 3988 and Millad NX8000 available from Milliken, may be used as they are.

Examples of the crystal nucleating agent other than the diacetal compounds include: carboxylate compounds such as sodium benzoate, aluminum p-t-butylbenzoate, metal cyclohexane dicarboxylates represented by the following formula (2), metal norbornane dicarboxylates represented by the following formula (3); phosphate compounds represented by the following formula (4); amide compounds represented by the following formula (5); and rosin compounds such as rosin acids represented by the following formula (6) or its metal salt compounds (e.g., alkali metal salts such as lithium, sodium, potassium, and magnesium salts).

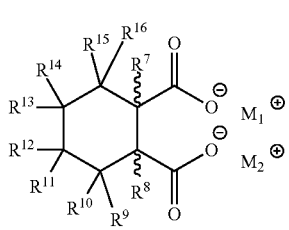

(2)

In the formula, $M_1$ and $M_2$ both represent a lithium ion or together represent single metal cations each independently selected from the group consisting of calcium, strontium, zinc, magnesium, and monobasic aluminum, $R^7$, $R^8$, $R^9$, $R^{10}$, $R^{11}$, $R^{12}$, $R^{13}$, $R^{14}$, $R^{15}$, and $R^{16}$ are the same as or different from one another and each selected from the group consisting of a hydrogen atom, a C1-C9 alkyl group (any of two vicinal (bonded to adjacent carbons) or geminal (bonded to the same carbon) alkyl groups may together form a hydrocarbon ring containing at most 6 carbon atoms), a hydroxyl group, a C1-C9 alkoxy group, a C1-C9 alkyleneoxy group, an amino group, a C1-C9 alkyl amino group, a halogen atom (fluorine, chlorine, bromine, or iodine), and a phenyl group.

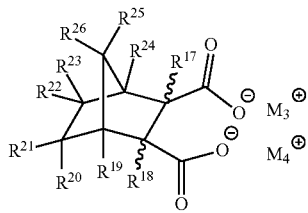

(3)

In the formula, $M_3$ and $M_4$ are the same as or different from each other and each independently selected from the group consisting of a metal cation and an organic cation or the two metal ions are put together as a single metal ion (divalent ion, for example, calcium), $R^{17}$, $R^{18}$, $R^{19}$, $R^{20}$, $R^{21}$, $R^{22}$, $R^{23}$, $R^{24}$, $R^{25}$, and $R^{26}$ are each independently selected from the group consisting of a hydrogen atom, a C1-C9 alkyl group, a hydroxyl group, a C1-C9 alkoxy group, a C1-C9 alkyleneoxy group, an amino group, a C1-C9 alkyl amino group, a halogen atom, a phenyl group, an alkyl phenyl group, and a geminal or vicinal carbon ring containing at most 9 carbon atoms, and the metal cation is preferably selected from the group consisting of calcium, strontium, barium, magnesium, aluminum, silver, sodium, lithium, rubidium, and potassium.

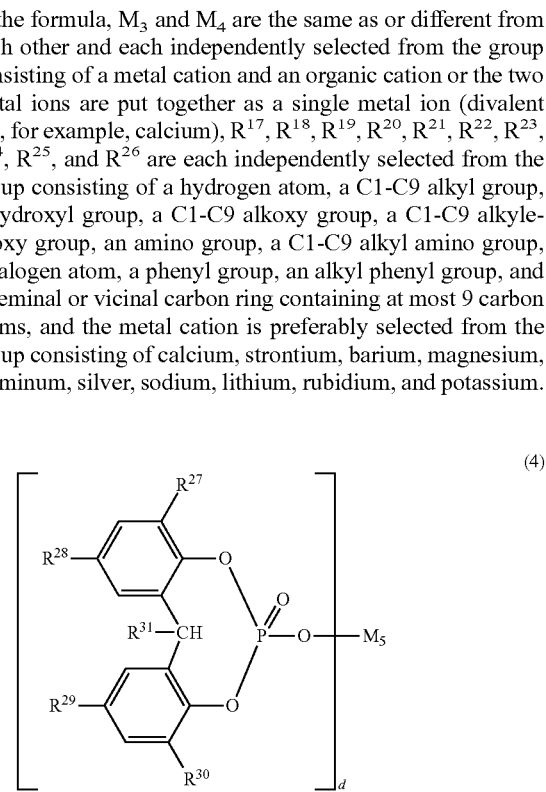

(4)

In the formula, $R^{27}$ to $R^{30}$ are the same as or different from each other and each represent a hydrogen atom or a C1-C9 alkyl group, $R^{31}$ represents a hydrogen atom or a C1-C3 alkyl group, d represents an integer of 1 or 2, and M5 represents an alkali metal when d represents 1 and represents an alkaline earth metal, zinc, or hydroxy aluminum when d represents 2.

(5)

In the formula, f represents an integer of 2 to 6, $R^{32}$ represents a C2-C18 saturated or unsaturated aliphatic polycarboxylic acid residue, a C3-C18 alicyclic polycarboxylic acid residue, or a C6-C18 aromatic polycarboxylic acid residue, 2 to 6 $R^{33}$s are the same as or different from each other and each represent a C5-C30 saturated or unsaturated aliphatic amine residue, a C5-C30 alicyclic amine residue, or a C6-C30 aromatic amine residue.

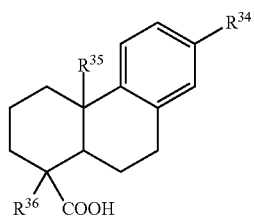

(6)

In the formula, $R^{34}$, $R^{35}$, and $R^{36}$ may be the same as or different from one another and each represent a hydrogen atom, an alkyl group, a cycloalkyl group, or an aryl group.

The bulk density may be adjusted to a certain range by any method as long as the effect of the present invention can be achieved. For example, a removable compound having a binder effect is preliminarily mixed with a crystal nucleating agent for polyolefin resins obtained by a conventional production method (hereafter, referred to as "a starting powder of a crystal nucleating agent for polyolefin resins") and granulated by extrusion or the like. The mixed compound having a binder effect is removed from the obtained granule so that parts where the compound having a binder effect has been present become void, thereby lowering the bulk density compared to a conventional granulation product in a similar shape.

For another example, the starting powder of a crystal nucleating agent for polyolefin resins is not formed into a complete granule. The starting powder in a powder state or a partly flaky state is only subjected to compression treatment. Thus, the bulk density can be adjusted. The "starting powder of a crystal nucleating agent for polyolefin resins" is only required to be a crystal nucleating agent for polyolefin resins obtained by a conventional production method, and the size, shape, type of the compound, and the like are not particularly limited.

The crystal nucleating agent of the present invention is preferably a granule obtained by preparing an extrusion-granulation product of a mixture containing the starting powder of a crystal nucleating agent for polyolefin resins and a compound having a binder effect and removing the compound having a binder effect from the extrusion-granulation product. It is commonly known that a smaller particle size is likely to cause a concern about the fluidity. Granulation has been confirmed to significantly improve the fluidity. More specifically, from the above standpoint, the obtained granular crystal nucleating agent preferably has a bulk density satisfying the above range and a powdering rate described later satisfying a certain range. The word "granular" herein refers to the shape having a size sufficient for improving the fluidity described below, i.e., having a specific bulk density, and being not easily powdered, i.e., having a specific powdering rate. Such a granular crystal nucleating agent is easily obtainable by, for example, mixing a crystal nucleating agent powder obtained by a conventional production method with a compound having a binder effect, granulating the mixture by extrusion, and removing the mixed compound having a binder effect.

According to the present inventors' findings, the bulk density described above and the powdering rate described later can be favorably set each within a certain range by granulating a mixture containing a starting powder of a crystal nucleating agent for polyolefin resins and a specific compound having a binder effect at a specific ratio by extrusion under a specific condition and removing the added compound, which enables production of a granular crystal nucleating agent for polyolefin resins in which the dispersibility in resin is improved without addition of a binder. The obtained granular crystal nucleating agent for polyolefin resins has highly excellent fluidity, does not cause a problem such as caking, and shows excellent dispersibility or solubility in resin. Moreover, a polyolefin resin composition containing the crystal nucleating agent and a molded article thereof has highly excellent transparency. The compound having a binder effect is removed from the crystal nucleating agent obtained by the above method, and therefore, the crystal nucleating agent is substantially free from a binder compound. Thus, a problem of caking or the like, which has disadvantageously occurred in a conventional granular crystal nucleating agent for polyolefin resins containing a binder compound, is solved and the applications of the crystal nucleating agent are widened.

The crystal nucleating agent of the present invention preferably has a powdering rate within a certain range. With a large powdering rate, the granule tends to be pulverized upon actual use thereof and the fluidity improving effect by granulation is not likely to be achieved. Also from the standpoint of the dispersibility or solubility in resin, it is important to set the powdering rate within a certain range. With an excessively high powdering rate, the granular crystal nucleating agent may be pulverized during the transport thereof or upon addition to a polyolefin resin, which may not only lower the fluidity but also causes a problem of dust or the like. In such a case, the value of the bulk density described above is commonly small.

Here, the powdering rate is an indication of the hardness of the granule obtained by the granulation. In the present invention, the powdering rate is obtained as follows. A specific impact is given to the granule, and the weight of the granule pulverized to a specific particle size or smaller is measured. The ratio of the obtained weight to the total weight of the granule before application of the impact is calculated, and the obtained value is taken as the powdering rate. Specifically, a sample used is preliminarily sieved through a 600-μm sieve. To the sample put on the 600-μm sieve is given vibration for a predetermined time. After the vibration stopped, the weight of the sample having passed through the 600-μm sieve during the vibration is measured. The obtained weight is divided by the total weight of the sample put onto the 600-μm sieve before the vibration started, and the quotient is centuplicated. The resulting value is taken as the powdering rate (%). With a higher powdering rate, the granule is fragile and pulverized with a slight impact. Such granule tends to be powdered before mixing with resin and the maintenance of the granular shape is difficult. As a result, the effect of improving the fluidity is not likely to be achieved. Though it depends on the type of the crystal nucleating agent, from the standpoint of the fluidity improving effect, the powdering rate is preferably 40% or lower, more preferably 30% or lower, still more preferably 20% or lower, particularly preferably 10% or lower in the present invention. With too low a powdering rate, the dispersibility or solubility in resin tends to be lowered. However, depending on the choice of the crystal nucleating agent or the compound having a binder effect, the dispersibility or solubility in resin is not necessarily lowered even when the powdering rate is lowered.

The granulation size is different according to the type of the crystal nucleating agent or the intended application and is difficult to determine unconditionally. Preferably, the recommended diameter after the granulation and the removal of the compound having a binder effect is 0.5 mm or larger.

The dispersibility or solubility in resin may be influenced by the particle size after the granulation. For example, in the case where the granule has a cylindrical shape, the recommended diameter thereof is preferably 5.0 mm or smaller, more preferable 2.5 mm or smaller, still more preferably 1.5 mm or smaller from the standpoint of the dispersibility or solubility in resin.

The diameter can be easily measured by a method of measuring the diameter of the obtained cylindrical granule using a caliper or the like.

<Compound Having a Binder Effect>

The compound having a binder effect in the present invention refers to a compound having an effect of promoting pressure bonding between particles of the starting powder of a crystal nucleating agent for polyolefin resins. Specifically, it is preferably a compound having an effect of wetting the surface of the starting powder of a crystal nucleating agent for polyolefin resins, swelling the starting powder of a crystal nucleating agent for polyolefin resins, or partly dissolving the starting powder of a crystal nucleating agent for polyolefin resins.

The compound having a binder effect to be used may have any structure as long as it exerts the effect of the present invention. For fulfilling the purpose of the present invention, it needs to be a compound easily removable after the granulation.

Specific examples thereof in the case where the compound is removed by drying (drying method) include: lower alcohols such as methanol, ethanol, propanol, butanol, and pentanol; low-boiling-point hydrocarbon compounds such as hexane and cyclohexane; ketone compounds such as acetone and methyl ethyl ketone; ether compounds such as dioxane; and water. These may be used alone or in combination.

Preferred among these is a C1-C4 alcohol, water, or a mixture of the alcohol and water. The alcohol is more preferably methanol and/or ethanol. In particular, most preferred is methanol or a mixture of methanol and water. In the case of a mixture of methanol and water, the proportion of methanol in the mixture is preferably 5% by weight or more, more preferably 10% by weight or more, still more preferably 30% by weight or more, particularly preferably 50% by weight or more.

In the case where the removal method is a method other than the above method, such as extraction described later or the like, also usable are glycerin, liquid paraffin, paraffin wax, fatty acids, and higher alcohols.

The amount of the compound having a binder effect to be mixed with the starting powder of a crystal nucleating agent for polyolefin resins is not particularly limited as long as the effect of the present invention is exerted, and cannot be determined unconditionally because it depends on the type of each compound or the granulation conditions.

The recommended amount of the compound having a binder effect relative to 100 parts by weight of the starting powder of a crystal nucleating agent for polyolefin resins is preferably 20 to 60 parts by weight, more preferably 30 to 50 parts by weight, still more preferably 40 to 50 parts by weight.

When the amount of the compound having a binder effect is less than 20 parts by weight, granulation tends to be difficult, and forcible granulation may lower the dispersibility or solubility in resin. When the amount of the compound having a binder effect is more than 60 parts by weight, the improving effect commensurate with the amount is hardly achieved and the powdering rate may be increased. Thus, the amount of less than 20 parts by weight and the amount of more than 60 parts by weight are both unfavorable.

The crystal nucleating agent of the present invention is preferably a compression product resulting from dry-compression because the bulk density described above can be favorably adjusted within a certain range. Such a crystal nucleating agent can be easily obtained by dry-compressing the starting powder of a crystal nucleating agent for polyolefin resins.

As a result of intensive studies for finding a method of not at all using any additive that is a heterologous component, the present inventors found out that a crystal nucleating agent produced by a specific method and having specific properties favorably satisfies the bulk density described above without essentially using any additive, and the fluidity thereof can be significantly improved without markedly lowering the dispersibility or solubility in resin which have been a problem.

While conventional compressive granulation is the operation for granulation, i.e., for producing a large and hard granule, the dry compression is the operation for exclusively performing compression of the starting powder of a crystal nucleating agent for polyolefin resins in a powder or partly flaky state, not for forming the starting powder of a crystal nucleating agent for polyolefin resins into a complete granule. Accordingly, the crystal nucleating agent of the present invention obtained by the dry compression is a compression product in a powder or fragile flaky state partly including coarse particles, having characteristics totally different from a granule obtainable by conventional compressive granulation.

The starting powder of a crystal nucleating agent for polyolefin resins used for the dry compression may have any shape as long as the effect of the present invention is exerted. It is particularly recommended to be a powder having an average particle size of preferably less than 15 μm, more preferably 10 μm or less. With such a shape, the dispersibility or solubility of the dry-compressed crystal nucleating agent in polyolefin resins tends to be favorably affected.

<Production of Crystal Nucleating Agent for Polyolefin Resins>

The production method of the crystal nucleating agent of the present invention is specifically described in the following with reference to a specific example. It is to be noted that the present invention is not necessarily limited to the following method as long as the aimed properties can be achieved.

The crystal nucleating agent of the present invention can be produced by a production method including the following steps (i) to (iii).

Step (i): The starting powder of a crystal nucleating agent for polyolefin resins and the compound having a binder effect are mixed to prepare a mixture.

Step (ii): The mixture obtained in the step (i) is granulated to provide a granulation product.

Step (iii): The compound having a binder effect blended in the step (i) is removed from the granulation product obtained in the step (ii). The present invention also encompasses the production method of the crystal nucleating agent for polyolefin resins of the present invention including such steps (i) to (iii).

The mixing method in the step (i) is not limited as long as the starting powder of a crystal nucleating agent for polyolefin resins and the compound having a binder effect can be uniformly mixed. An exemplary method includes mixing using a stirring mixer, a screw mixer or the like at room temperature or under heating at 100° C. or lower for several to several tens of minutes.

In the step (i), the amount of the compound having a binder effect relative to the starting powder of a crystal nucleating agent for polyolefin resins is not particularly limited as long as the effect of the present invention is exerted, and cannot be determined unconditionally because it depends on the type of each compound or the granulation condition. The recommended amount of the compound having a binder effect relative to 100 parts by weight of the starting powder of a crystal nucleating agent for polyolefin resins is preferably 20 to 60 parts by weight, more preferably 30 to 50 parts by weight, still more preferably 40 to 50 parts by weight. When the amount of the compound having a binder effect is less than 20 parts by weight, the granulation tends to be difficult, and forcible granulation may lower the dispersibility or solubility in resin. When the amount of the compound having a binder effect is more than 60 parts by weight, the improving effect commensurate with the amount is hardly achieved and the powdering rate may be increased. Thus, the amount of less than 20 parts by weight and the amount of more than 60 parts by weight are both unfavorable.

The granulation method in the step (ii) is not limited as long as the mixture can be granulated, and extrusion granulation is recommended. In the extrusion granulation, a raw material, the mixture obtained in the step (i) in the present invention, is compressed using a screw, a plunger, a roller, or the like to be extruded in a cylindrical shape laterally or downward from a screen die having a large number of pores of a predetermined size. Thus, granulation is carried out. The cylindrical granulation product is cut at an appropriate length using a cutter or the like, thereby obtaining a granule. The obtained granule can be further shaped using a shaping machine or the like.

The extrusion method is not particularly limited as long as the granule that can exert the effect of the present invention can be obtained. In consideration of the productivity or the like, the downward extrusion using a roller is most efficient.

The extrusion granulation is commonly performed at room temperature but may be performed under low-temperature heating at 100° C. or lower.

The pore size of the screen die is not particularly limited as long as it falls within a range that provides a granule exerting the effect of the present invention. In consideration of the balance between the fluidity and the dispersibility or solubility in resin, the screen die having a pore size of preferably about 0.5 to 5.0 mm in diameter is recommended. The recommended screen die more preferably has a pore size of about 0.5 to 2.5 mm in diameter, still more preferably about 0.5 to 1.5 mm in diameter. With such a die, the effect of the present invention can be most exerted.

The pressure for extrusion depends on the pore size of the screen die and cannot be limited unconditionally. Too low a pressure tends to lower the productivity and too high a pressure may make the resulting granule too hard, possibly affecting the dispersibility or solubility thereof in polyolefin resins.

In the case where the extruded granulation products are connected in series, a cutter or the like can be provided directly after the screen die to adjust the lengths of the granulation products appropriately before supplying them to the next step.

The removal method in the step (iii) may be any method that can remove the compound having a binder effect mixed in the step (i). Specifically, the method is different depending on the type of the compound having a binder effect and a method appropriate for the type is employed. For example, in the case where a lower alcohol having a relatively low boiling point is used, a so-called drying method in which removal is performed under heating and/or pressurization is commonly employed. In the case where a compound having a high boiling point and is not easily removable is used, a so-called extraction method in which a solvent that dissolves the compound having a binder effect alone is used for the removal may be employed.

In the case of the drying method, setting of the condition so as not to cause coloring or the like is important. The recommended condition is preferably 150° C. or lower, more preferably 120° C. or lower. In the case where the removal is difficult, the method of reducing the pressure is also effective.

After the step (iii), optional addition of a sizing step or a classification step is also effective. For example, regulation of the particle shape using a general-purpose sieve or an airflow classifying apparatus enables more efficient exertion of the effect of the present invention.

The crystal nucleating agent of the present invention can be also produced by dry compression. The present invention also encompasses a production method of the crystal nucleating agent for polyolefin resins of the present invention by such dry compression.

Examples of the dry compression method include a tablet method and a roller compression method. For more precise control of the compression state, a roller compression method is recommended. The device used for roller compression may be a commonly used device. Specific examples thereof include a compactor available from Hosokawa Micron Corporation and a roller compactor available from Freund Corp.

More specifically, in the roller compression method for example, the feed of the starting powder of a crystal nucleating agent for polyolefin resins, inter-roll distance, roll speed, roll pressure, and the like are adjusted for dry compression of the starting powder of a crystal nucleating agent for polyolefin resins. Among these, the roll pressure is important, and is recommended to be adjusted within a range of preferably 0.1 to 10 MPa, more preferably 1 to 10 MPa, still more preferably 3 to 10 MPa. When the roll pressure is less than 0.1 MPa, the improvement of the fluidity may be insufficient. When the roll pressure is more than 10 MPa, the dispersibility may be lowered.

The shape of the crystal nucleating agent of the present invention is not particularly limited as long as the effect of the present invention is exerted, and may have a powdery shape or a flaky shape (scaly shape).

In the case where the crystal nucleating agent of the present invention has a flaky shape, it may be further pulverized or crushed to be powdered before use. The fluidity is improved even when the flaky shape of the crystal nucleating agent is maintained. However, in the case where the dispersibility or solubility in polyolefin resins is an important factor, pulverizing or crushing before use is more preferred.

Moreover, in the case where the flaky crystal nucleating agent of the present invention is pulverized or crushed before use, the resulting crystal nucleating agent more preferably contains coarse particles at a certain proportion in terms of the fluidity. For example, in a particularly recommended embodiment, the proportion of coarse particles having a particle size of 15 µm or larger is preferably 50 vol % or more, more preferably 60 vol % or more relative to the total volume of the crystal nucleating agent in the laser diffraction particle size distribution measurement. With the proportion of the coarse particles of 50 vol % or more, the fluidity of the entire crystal nucleating agent including finer particles is presumably improved.

The pulverization or crushing can be performed using a commonly used pulverizer or crusher, such as a hammer mill, a pin mill a jet mill, a pulverizer, a cutter mill, a planar crusher, or a flake crusher. After the pulverization or crushing, the classification may be optionally carried out using a general-purpose classifying device such as a screen classifier (e.g., a vibration sieve, cylindrical stirring sieve) or a wind force classifier (e.g., forced centrifugation, gravitational inertia classification).

The laser diffraction particle size distribution measurement can be performed using a common device by a common method under a common condition. For example, using a laser diffraction particle size distribution analyzer ("Mastersizer 3000" available from Malvern Instruments), a sample is dispersed in an aqueous solution containing a surfactant as a dispersant by sufficient stirring in a wet measurement cell, the resulting mixture is further stirred and circulated in the analyzer and uniformly dispersed in the analyzer under irradiation with ultrasonic wave, and the particle size distribution of the sample can be measured under irradiation with ultrasonic wave.

The crystal nucleating agent of the present invention obtained by the dry compression has a feature of very low secondary aggregation properties. The feature is presumably owing to the dry compression according to the present invention. In the present invention, the secondary aggregation properties are determined based on the amount of the secondary aggregate of a predetermined size or larger generated during the sieve analysis. Specifically, the sieve analysis is carried out under the condition in conformity with section 6.1 of JIS K 0069 (1992), and the proportion of the weight of residues left on the JIS test sieve having an aperture of 1 mm relative to the total weight of the sample is obtained. In the sieve analysis, since the secondary aggregation properties are determined based on the amount of the secondary aggregate generated during the sieve analysis, no brush is used and manual sieving is performed in which the sieving time is set to one minute under the condition that the secondary aggregate on the sieve is not crushed. The effectiveness of the evaluation method of the secondary aggregation properties is confirmed as follows. Manual sieving of a sample of the same starting powder of a crystal nucleating agent for polyolefin resins was performed under the condition that the secondary aggregate was not left, and the amount of residues left on the sieve having an aperture of 1 mm or larger was obviously smaller than the amount of the above secondary aggregate, showing a significant difference. In addition, this analysis was found to be generally reproducible. Accordingly, when more residues are left on the sieve, secondary aggregation properties are greater. Moreover, when the proportion obtained from the result of the sieve analysis is preferably 25% by weight or less, more preferably 20% by weight or less, the fluidity is considered to be practically acceptable as a whole.

<Method for Improving Fluidity of Crystal Nucleating Agent for Polyolefin Resins>

The present invention also encompasses a method for improving the fluidity of a crystal nucleating agent for polyolefin resins, including adjusting the nucleating agent to have an aerated bulk density within a range of 0.25 to 0.50 g/cm$^3$, a packed bulk density within a range of 0.3 to 0.80 g/cm$^3$, and a powdering rate of 40% or lower.

The present invention further relates to a method for improving the fluidity of a crystal nucleating agent for polyolefin resins, including a dry compression step by a roller compression method. As the roll pressure in the compression processing or the like, those mentioned for the production of the crystal nucleating agent for polyolefin resins are favorably employed.

<Polyolefin Resin Composition>

The present invention also relates to a polyolefin resin composition containing a polyolefin resin and the crystal nucleating agent for polyolefin resins of the present invention or a crystal nucleating agent for polyolefin resins produced by the production method of a crystal nucleating agent for polyolefin resins of the present invention. The composition can be easily obtained by dry-blending the crystal nucleating agent of the present invention, a polyolefin resin, and optionally other additive(s) for polyolefin resins at room temperature and then melt-mixing them under a predetermined condition.

The concentration of the crystal nucleating agent of the present invention in the polyolefin composition is not limited as long as it can exert an effect as the crystal nucleating agent according to the present invention. The concentration relative to 100 parts by weight of the polyolefin resin is preferably 0.001 to 10 parts by weight, more preferably 0.01 to 5 parts by weight.

[Polyolefin Resin]

The polyolefin resin is not particularly limited as long as the effect of the present invention is exerted, and conventionally known polyolefin resins are usable. Examples thereof include polyethylene resins, polypropylene resins, polybutene resins, polymethylpentene resins, and polybutadiene resins. More specific examples thereof include high-density polyethylene, medium-density polyethylene, linear polyethylene, ethylene copolymers having an ethylene content of 50% by weight or higher, preferably 70% by weight or higher, propylene homopolymers, propylene copolymers having a propylene content of 50% by weight or higher, preferably 70% by weight or higher, butene homopolymers, butene copolymers having a butene content of 50% by weight or higher, preferably 70% by weight or higher, methylpentene homopolymers, methylpentene copolymers having a methylpentene content of 50% by weight or higher, preferably 70% by weight or higher, and polybutadiene. The above copolymers each may be a random copolymer or a block copolymer. Moreover, in the case where these resins are each a stereoregular resin, it may be an isotactic resin or a syndiotactic resin. Specific examples of comonomers that can constitute the copolymers include: C2-C12 α-olefins such as ethylene, propylene, butene, pentene, hexene, heptene, octene, nonene, decene, undecene, and dodecene; bicyclo monomers such as 1,4-endomethylenecyclohexane; (meth)acrylates such as methyl (meth)acrylate and ethyl (meth)acrylate; and vinyl acetate.

Examples of the catalyst usable for production of the polymer include, in addition to commonly used ziegler-natta catalysts, catalyst systems combining a catalyst including a carrier containing magnesium halides (e.g., magnesium chloride) and a transition metal compound (e.g., titanium halides such as titanium trichloride and titanium tetrachloride) supported on the carrier with an alkyl aluminum compound (e.g., triethyl aluminum, diethyl aluminum chloride), and metallocene catalysts.

The melt flow rate (hereafter, abbreviated as "MFR", JIS K 7210-1999) of the polyolefin resin according to the present invention is selected as appropriate according to the molding method employed. The recommended MFR is commonly about 0.01 to 200 g/10 min, preferably about 0.05 to 100 g/10 min.

[Other Additives]

As described above, the polyolefin resin composition of the present invention may contain other additive(s) for polyolefin resins according to the intended use or application thereof, within a range that the effect of the present invention is not impaired.

Examples of the additive for polyolefin resins include various additives listed in "The Tables of Positive Lists of Additives" edited by Japan Hygienic Olefin And Styrene Plastics Association (January, 2002). Specific examples of the various additives include fluorescent brighteners (e.g., 2,5-thiophene diyl(5-tert-butyl-1,3-benzoxazole), 4,4'-bis (benzoxazol-2-yl)stilbene), antioxidants, stabilizers (e.g., metal compounds, epoxy compounds, nitrogen compounds, phosphorus compounds, sulfur compounds), ultraviolet absorbers (e.g., benzophenone compounds, benzotriazole compounds), surfactants, lubricants (e.g., aliphatic hydrocarbons such as paraffin and wax, C8-C22 higher fatty acids, C8-C22 higher fatty acid metal (Al, Ca) salts, C8-C22 higher aliphatic alcohols, polyglycol, esters of C4-C22 higher fatty acids and C4-C18 aliphatic monovalent alcohols, C8-C22 higher fatty acid amides, silicone oil, rosin derivatives), fillers (e.g., talc, hydrotalcite, mica, zeolite, perlite, diatom earth, calcium carbonate, glass fiber), foaming agents, foaming aids, polymer additives, plasticizers (e.g., dialkylphthalate, dialkylhexahydrophthalate), crosslinking agents, crosslinking accelerators, antistatic agents, flame retardants, dispersants, organic/inorganic pigments (e.g., indigo compounds, phthalocyanine compounds, anthraquinone compounds, ultramarine compounds, cobalt aluminate compounds), processing aids, and other crystal nucleating agents.

In the case where any of these additives is used, it may be used in a usual amount as long as the effect of the present invention is not disturbed. For example, the amount relative to 100 parts by weight of the polyolefin resin is normally preferably about 0.0001 to 100 parts by weight, more preferably about 0.001 to 50 parts by weight.

Examples of the antioxidant include phenolic antioxidants, phosphite antioxidants, and sulfur antioxidants. Specific examples of the antioxidants include: phenolic antioxidants such as 2,6-di-tert-butylphenol, tetrakis[methylene-3-(3,5-tert-butyl-4-hydroxyphenol)propionate]methane, and 2-hydroxy-4-methoxybenzophenone; sulfur antioxidants such as alkyl disulfide, thiodipropionates, and benzothiazole; and phosphite antioxidants such as tris(nonylphenyl) phosphite, diphenyl isodecyl phosphite, triphenyl phosphite, tris(2,4-di-tert-butylphenyl)phosphite, and 3,9-bis(2,6-tert-butyl-4-methylphenoxy)-2,4,8,10-tetraoxa-3,9-diphosphaspiro[5,5]undecane. Among these, particularly recommended are tetrakis[methylene-3-(3,5-di-t-butyl-4-hydroxyphenyl)propionate]methane that is a phenolic antioxidant, and tris(2,4-di-tert-butylphenyl)phosphite and 3,9-bis(2,6-tert-butyl-4-methylphenoxy)-2,4,8,10-tetraoxa-3,9-diphosphaspiro[5,5]undecane that are phosphite antioxidants.

<Polyolefin Resin Molded Article>

The present invention also relates to a polyolefin resin molded article that is produced using the polyolefin resin composition of the present invention as a raw material. The polyolefin resin molded article of the present invention is obtainable by molding the polyolefin resin composition of the present invention by a commonly used molding method. The molding method is not particularly limited as long as the effect of the present invention is exerted. Any of conventionally known molding methods such as injection molding, extrusion molding, blow molding, pressure molding, rotational molding, and film molding may be employed.

The polyolefin resin molded article obtained as above is excellent in optical characteristics (e.g., transparency) and mechanical properties (e.g., impact resistance) and is very useful for various applications including automobile parts, electric parts, machine components, and commodities in the form of a molded article, a sheet, or a film.

EXAMPLES

The present invention is more specifically described in the following with reference to, but not limited to, the examples. The abbreviations of the compounds used in examples and application examples, and the measurement process of each property are mentioned below.

[Characteristics of Crystal Nucleating Agent for Polyolefin Resins]

(1) Measurement of Bulk Density

A funnel was perpendicularly held at a position of 2 cm above the opening section of a 100-cm³ measuring cylinder with its axis aligned with the axis of the measuring cylinder. A crystal nucleating agent in an amount of 100 cm³ was slowly (without pressurization) put into the 100-cm³ measuring cylinder through the funnel. The weight of the crystal nucleating agent in the measuring cylinder was measured to 0.1-g units using a scale. The aerated bulk density was obtained by the following equation (1) using the obtained weight. Subsequently, the measuring cylinder was vertically dropped onto a rubber sheet from a height of 5 cm (tapping) for 50 times. The volume of the crystal nucleating agent in the measuring cylinder was read to 0.1-cm³ units, and the packed bulk density was obtained using the following equation (2).

Aerated bulk density (g/cm³)=Weight of crystal nucleating agent in measuring cylinder (g)/100 cm³     Equation (1):

Packed bulk density (g/cm³)=Weight of crystal nucleating agent in measuring cylinder (g)/Volume of crystal nucleating agent after tapping (cm³)     Equation (2):

(2) Powdering Rate

A sample in an amount of 10 g was slowly put onto a 600-μm sieve, and vibrated for 30 minutes. After the vibration stopped, the weight of the sample having passed through the 600-μm sieve was measured, and the powdering rate (%) was obtained using the following equation.

Powdering rate (%)=Weight of sample having passed through sieve (g)/weight of sample put onto sieve (g)×100

The sample was preliminarily sieved through a sieve having the same aperture as that of the sieve used in the test and only the sample left on the sieve was used as the sample for the measurement of the powdering rate. Accordingly, the powder passing through the sieve during the test was all powdered during the test.

(3) Powder Fluidity Test (Funnel Test)

The crystal nucleating agent was fed into a funnel having a conical part with a diameter of 15 cm and a tube with a diameter of 1.5 cm from the height of 5 cm above the upper edge of the funnel, and dropped through a lower outlet without vibration. The fluidity of the crystal nucleating agent was evaluated based on the discharge state of the crystal nucleating agent from the funnel on a four-point scale in accordance with the following criteria.

(Evaluation Criteria)

Excellent: The entire crystal nucleating agent was immediately discharged from the funnel and almost no deposition was found on the inner wall of the funnel.

Good: The crystal nucleating agent was slightly left in the funnel without being discharged but the residual crystal nucleating agent in the funnel was entirely discharged with application of a small impact.

Fair: The crystal nucleating agent was left in the funnel without being discharged and complete discharge of the residual crystal nucleating agent in the funnel was difficult only with application of a small impact.

Poor: A large amount of the crystal nucleating agent was left in the funnel without being discharged and discharge of the residual crystal nucleating agent in the funnel was difficult even with application of an impact.

(4) Sieve Analysis

Sieve analysis was carried out under the condition in conformity with section 6.1 of JIS K 0069 (1992), and the proportion of the weight of the residue on the JIS test sieve having an aperture of 1 mm relative to the total weight of the sample was measured. In the sieve analysis, no brush was used and manual sieving was performed in which the sieving time was set to one minute under the condition that the secondary aggregate on the sieve was not crushed. Sieving of the crystal nucleating agent of the present invention in each example described later was preliminarily performed under the condition that the secondary aggregate was not left, and the amount of the residue left on the sieve having an aperture of 1 mm was confirmed to be smaller than 1% by weight. In the case of a starting powder of a crystal nucleating agent for polyolefin resins in a comparative example described later, the amount of the residue on the sieve was confirmed to be 0% by weight. Accordingly, the amount of the residue on the sieve is useful as an indication of the amount of the secondary aggregate generated in a certain period of time. When the amount of the residue on the sieve is larger, the secondary aggregation properties are considered to be higher.

(5) Measurement of Angle of Repose

Under the conditions of a temperature of 25° C. and a humidity of 60%, the crystal nucleating agent in an amount of 30 g was fed into a funnel having a conical part with a diameter of 9 cm and a tube with a diameter of 1 cm from the height of 1 cm above the upper edge of the funnel, and dropped without vibration onto a circular stage with a diameter of 9 cm placed 10 cm below the lower outlet of the funnel. The height of the conical deposition of the dropped crystal nucleating agent was measured, and the angle formed between the horizontal plane and the generatrix was obtained by calculation as the angle of repose (unit: degree). A smaller angle of repose indicates better powder fluidity.

[Characteristics of Molded Article]

(6) Measurement of Haze Value

The haze value was measured using a haze meter available from Toyo Seiki Seisakusho, Ltd. by a method in conformity with JIS K 7136 (2000). The evaluation sample used was a polypropylene resin molded article that was a 1-mm-thick injection molded article. A smaller haze value indicates better transparency.

(7) Evaluation of White Spots

The evaluation sample used was a polyolefin resin molded article (50 mm×50 mm×1 mm) obtained by injection molding. The number of white spots in the molded article was visually counted. The numbers of white spots on five sheets of the samples was averaged, and the obtained value was used as the number of white spots of the sample. The obtained results were classified and rated on a 3-point scale. Excellent: The number of white spots is less than 3. No problems at all in terms of the performance of the molded article.
Good: The number of white spots is within a range of 3 to 15. No problems in terms of the performance as the nucleating agent but there may possibly be an influence of an undispersed matter in terms of other physical properties.
Poor: The number of white spots is more than 15. The effect in terms of the performance as the nucleating agent is obviously insufficient and an undispersed matter may highly possibly cause a problem in terms of various physical properties.

Abbreviations of Compounds in Examples
DMDBS: 1,3:2,4-bis-O-(3',4'-dimethylbenzylidene)-D-sorbitol
EDBS: 1,3:2,4-bis-O-(p-ethylbenzylidene)-D-sorbitol
CDBS: 1,3:2,4-bis-O-(p-chlorobenzylidene)-D-sorbitol
PDBN: 1,3:2,4-bis-O-(p-n-propylbenzylidene)-1-n-propyl-sorbitol Examples 1 to 12

Step (i): A universal stirring mixer (5dmv-01-rr available from Dalton Corporation, capacity of 4.7 L) equipped with a thermometer and a condenser was charged with DMDBS that is a powdered crystal nucleating agent for polyolefin resins and methanol that is a compound having a binder effect or a solution mixture containing methanol and water each in an amount as specified in Table 1, followed by stirring at room temperature for 10 minutes. Thus, a mixture of the crystal nucleating agent for polyolefin resins and the compound having a binder effect was obtained.

Step (ii): Subsequently, to a fine disc pelleter PV-5 (available from Dalton Corporation) including a screen die with a pore size of 1.0 mm was gradually fed the obtained mixture such that the load was constant at room temperature, and extrusion granulation was carried out, thereby obtaining a granulation product.

Step (iii): Then, the obtained granulation product was dried at 120° C. in vacuo for one hour so that the methanol or the mixture of methanol and water was removed.

Classification step: After the removal of the compound having a binder effect, the granulation product was classified using a sieve having an aperture of 600 μm to remove a small granulation product and an ungranulated powder. Thus, the granular crystal nucleating agent for polyolefin resins of the present invention was obtained. The diameter of the granulation product was measured using a caliper, and was within a range of 0.8 to 1.2 mm.

The aerated bulk density, packed bulk density, and powdering rate of the obtained granular crystal nucleating agent for polyolefin resins were measured. Table 1 shows the results. Subsequently, the evaluation of the powder fluidity by the powder fluidity test (funnel test) was performed on the obtained granular crystal nucleating agent for polyolefin resins. Table 1 shows the results.

Next, 100 parts by weight of a polypropylene random copolymer (MFR=7 g/10 min (load: 2160 g, temperature: 230° C.), R-720 available from Prime Polymer Co., Ltd.) as a polyolefin rein, 0.2 parts by weight of the obtained granular crystal nucleating agent for polyolefin resins as a crystal nucleating agent, and 0.05 parts by weight of calcium stearate (CaSt), 0.01 parts by weight of tetrakis [methylene-3-(3,5-di-t-butyl-4-hydroxyphenyl)propionate]methane (Irg1010), and 0.05 parts by weight of tetrakis (2,4-di-t-butylphenyl)phosphite (available from BASF Japan Ltd., product name: "IRGAFOS168") as other additives were dry-blended. The dry-blended mixture was melted and mixed using a single screw extruder (VS-20 available from Tanabe Plastics Machinery Co., Ltd.) at a barrel temperature of 250° C., and the extruded strands were cooled and cut using a pelletizer. Thus, a polyolefin resin composition was prepared.

Next, the obtained polyolefin resin composition was molded using an injection molding apparatus (NS40-5A available from Nissei Plastic Industrial Co., Ltd.) under the conditions of an injection molding temperature (heating temperature) of 240° C. and a die temperature (cooling temperature) of 40° C. to provide a 1-mm-thick polyolefin resin molded article.

The obtained molded article was used as an evaluation sample in measurement of the haze value. Table 1 shows the results. The visual evaluation of white spots in the molded article by the above method was performed. Table 1 shows the results.

Comparative Example 1

Using DMDBS alone without blending a compound having a binder effect, extrusion granulation was carried out as in Example 1 in an attempt to produce a granular crystal nucleating agent for polyolefin resins. Though slight granulation was observed, the DMDBS was mostly in a powder state and the granulated part was very fragile and substantially cannot be treated as a granule. Accordingly, classification or like operation was not performed and it was taken as a crystal nucleating agent for polyolefin resins outside the present invention as it was.

The aerated bulk density and packed bulk density of the obtained crystal nucleating agent for polyolefin resins were measured. Table 1 shows the results. Subsequently, the evaluation of the powder fluidity by the powder fluidity test (funnel test) was performed on the obtained crystal nucleating agent for polyolefin resins. Table 1 shows the results.

Next, a polyolefin resin composition and a polyolefin resin molded article were obtained as in Example 1. The haze value of the obtained molded article was measured. Table 1 shows the result. The visual evaluation of white spots in the molded article was performed by the above method. Table 1 shows the result.

Comparative Example 2

The aerated bulk density and packed bulk density of DMDBS in a powder state before granulation were measured.

Table 1 shows the results. Subsequently, the evaluation of the powder fluidity by the powder fluidity test (funnel test) was performed as in the examples. Table 1 shows the result.

Next, a polyolefin resin composition and a polyolefin resin molded article were obtained as in Example 1. The haze value of the obtained molded article was measured. Table 1 shows the result. The visual evaluation of white spots in the molded article was performed by the above method. Table 1 shows the result.

TABLE 1

| | Example | | | | | | |
|---|---|---|---|---|---|---|---|
| | 1 | 2 | 3 | 4 | 5 | 6 | 7 |
| Composition in step (i) (parts by weight) | | | | | | | |
| DMDBS | 70 | 60 | 50 | 70 | 60 | 50 | 60 |
| Methanol | 30 | 40 | 50 | 21 | 28 | 35 | 20 |
| Water | — | — | — | 9 | 12 | 15 | 20 |
| (1) Characteristics of crystal nucleating agent | | | | | | | |
| Aerated bulk density (g/cm$^3$) | 0.40 | 0.40 | 0.41 | 0.39 | 0.41 | 0.40 | 0.41 |
| Packed bulk density (g/cm$^3$) | 0.43 | 0.44 | 0.45 | 0.43 | 0.45 | 0.44 | 0.45 |
| Powdering ratio (%) | 15.7 | 5.0 | 1.3 | 24.0 | 14.7 | 4.4 | 10.5 |
| Angle of repose (degrees) | 39 | 38 | 37 | 39 | 38 | 38 | 38 |
| Powder fluidity test | Excellent | Excellent | Excellent | Excellent | Excellent | Excellent | Excellent |
| (2) Evaluation of molded article | | | | | | | |
| Haze value | 5.7 | 5.7 | 5.6 | 5.8 | 5.7 | 5.7 | 5.7 |
| Evaluation of white spots | Excellent | Excellent | Excellent | Good | Excellent | Excellent | Excellent |

| | Example | | | | | Comparative Example | |
|---|---|---|---|---|---|---|---|
| | 8 | 9 | 10 | 11 | 12 | 1 | 2 |
| Composition in step (i) (parts by weight) | | | | | | | |
| DMDBS | 50 | 60 | 50 | 60 | 50 | 100 | — |
| Methanol | 25 | 12 | 15 | 4 | 5 | — | — |
| Water | 25 | 28 | 35 | 36 | 45 | — | — |
| (1) Characteristics of crystal nucleating agent | | | | | | | |
| Aerated bulk density (g/cm$^3$) | 0.41 | 0.40 | 0.40 | 0.40 | 0.40 | 0.24 | 0.20 |
| Packed bulk density (g/cm$^3$) | 0.46 | 0.43 | 0.44 | 0.44 | 0.41 | 0.34 | 0.31 |
| Powdering ratio (%) | 6.3 | 19.0 | 7.9 | 28.9 | 17.8 | — | — |
| Angle of repose (degrees) | 37 | 38 | 37 | 40 | 39 | 46 | 48 |
| Powder fluidity test | Excellent | Excellent | Excellent | Excellent | Excellent | Poor | Poor |
| (2) Evaluation of molded article | | | | | | | |
| Haze value | 5.6 | 5.7 | 5.7 | 5.8 | 5.7 | 6.2 | 5.8 |
| Evaluation of white spots | Excellent | Excellent | Excellent | Good | Good | Poor | Excellent |

Examples 13 to 24

The granular crystal nucleating agent for polyolefin resins of the present invention was obtained as in Example 1, except that a mixture of EDBS and DMDBS (mixing ratio: EDBS/DMDBS=7/3) was used as the crystal nucleating agent for polyolefin resins instead of DMDBS. The diameter of the granulation product measured using a caliper was within a range of 0.8 to 1.1 mm.

The aerated bulk density, packed bulk density, and powdering rate of the obtained granular crystal nucleating agent for polyolefin resins were measured. Table 2 shows the results. Subsequently, the evaluation of the powder fluidity by the powder fluidity test (funnel test) was performed on the obtained granular crystal nucleating agent for polyolefin resins. Table 2 shows the result.

Comparative Example 3

Using a mixture of EDBS and DMDBS (mixing ratio: EDBS/DMDBS=7/3) alone without blending a compound having a binder effect, extrusion granulation was performed as in Example 1 in an attempt to produce a granular crystal nucleating agent for polyolefin resins. Though slight granulation was observed, the mixture was mostly in a powder state and the granulated part was very fragile and substantially cannot be treated as a granule. Accordingly, classification or like operation was not performed and it was taken as a crystal nucleating agent for polyolefin resins outside the present invention as it was.

The aerated bulk density and packed bulk density of the obtained crystal nucleating agent for polyolefin resins were measured. Table 2 shows the results. Subsequently, the evaluation of the powder fluidity by the powder fluidity test (funnel test) was performed on the obtained crystal nucleating agent for polyolefin resins. Table 2 shows the result.

Next, a polyolefin resin composition and a polyolefin resin molded article were obtained as in Example 1. The haze value of the obtained molded article was measured. Table 2 shows the result. The visual evaluation of white spots in the molded article was performed by the above method. Table 2 shows the result.

Comparative Example 4

The aerated bulk density and packed bulk density of a mixture of EDBS and DMDBS (mixing ratio: EDBS/DMDBS=7/3) in a powder state before granulation were measured. Table 2 shows the results. Subsequently, the evaluation of the powder fluidity by the powder fluidity test (funnel test) was performed as in the examples. Table 2 shows the result.

Next, a polyolefin resin composition and a polyolefin resin molded article were obtained as in Example 13. The haze value of the obtained molded article was measured. Table 2 shows the result. Visual evaluation of white spots in the molded article was performed. Table 2 shows the result.

TABLE 2

| | Example | | | | | | |
|---|---|---|---|---|---|---|---|
| | 13 | 14 | 15 | 16 | 17 | 18 | 19 |
| Composition in step (i) (parts by weight) | | | | | | | |
| DMDBS | 24 | 21 | 18 | 15 | 21 | 18 | 15 |
| EDBS | 56 | 49 | 42 | 35 | 49 | 42 | 35 |
| Methanol | 20 | 30 | 40 | 50 | 21 | 28 | 35 |
| Water | — | — | — | — | 9 | 12 | 15 |
| (1) Characteristics of crystal nucleating agent | | | | | | | |
| Aerated bulk density (g/cm$^3$) | 0.38 | 0.40 | 0.41 | 0.41 | 0.39 | 0.41 | 0.41 |
| Packed bulk density (g/cm$^3$) | 0.41 | 0.42 | 0.44 | 0.45 | 0.42 | 0.43 | 0.43 |
| Powdering ratio (%) | 32.3 | 6.5 | 2.5 | 1.0 | 26.9 | 7.1 | 5.6 |
| Angle of repose (degrees) | 41 | 40 | 37 | 37 | 39 | 37 | 37 |
| Powder fluidity test | Excellent | Excellent | Excellent | Excellent | Excellent | Excellent | Excellent |
| (2) Evaluation of molded article | | | | | | | |
| Haze value | 7.4 | 7.3 | 7.4 | 7.4 | 7.3 | 7.4 | 7.3 |
| Evaluation of white spots | Good | Good | Excellent | Excellent | Good | Excellent | Excellent |

| | Example | | | | | Comparative Example | |
|---|---|---|---|---|---|---|---|
| | 20 | 21 | 22 | 23 | 24 | 3 | 4 |
| Composition in step (i) (parts by weight) | | | | | | | |
| DMDBS | 18 | 15 | 18 | 15 | 15 | 30 | — |
| EDBS | 42 | 35 | 42 | 35 | 35 | 70 | — |
| Methanol | 20 | 25 | 12 | 15 | 5 | — | — |
| Water | 20 | 25 | 28 | 35 | 45 | — | — |
| (1) Characteristics of crystal nucleating agent | | | | | | | |
| Aerated bulk density (g/cm$^3$) | 0.39 | 0.40 | 0.39 | 0.40 | 0.39 | 0.23 | 0.20 |
| Packed bulk density (g/cm$^3$) | 0.42 | 0.43 | 0.41 | 0.42 | 0.42 | 0.36 | 0.30 |
| Powdering ratio (%) | 32.3 | 8.1 | 39.4 | 20.3 | 22.8 | — | — |
| Angle of repose (degrees) | 38 | 37 | 38 | 38 | 39 | 47 | 48 |
| Powder fluidity test | Excellent | Excellent | Excellent | Excellent | Excellent | Poor | Poor |
| (2) Evaluation of molded article | | | | | | | |
| Haze value | 7.3 | 7.3 | 7.4 | 7.3 | 7.3 | 8.1 | 7.3 |
| Evaluation of white spots | Excellent | Excellent | Excellent | Excellent | Excellent | Poor | Excellent |

Examples 25 to 32

The granular crystal nucleating agent for polyolefin resins of the present invention was obtained as in Example 1, except that PDBN was used as the crystal nucleating agent for polyolefin resins instead of DMDBS. The diameter of the granulation product was measured using a caliper, and was within a range of 0.9 to 1.3 mm.

The aerated bulk density, packed bulk density, and powdering rate of the obtained granular crystal nucleating agent for polyolefin resins were measured. Table 3 shows the results. Subsequently, the evaluation of the powder fluidity by the powder fluidity test (funnel test) was performed on the obtained granular crystal nucleating agent for polyolefin resins. Table 3 shows the result.

Comparative Example 5

Using PDBN alone without blending a compound having a binder effect, extrusion granulation was performed as in Example 1 in an attempt to produce a granular crystal nucleating agent for polyolefin resins. Though slight granulation was observed, it was mostly in a powder state and the granulated part was very fragile and substantially cannot be treated as a granule. Accordingly, classification or like operation was not performed and it was taken as a crystal nucleating agent for polyolefin resins outside the present invention as it was.

The aerated bulk density and packed bulk density of the obtained crystal nucleating agent for polyolefin resins were measured. Table 3 shows the results. Subsequently, the evaluation of the powder fluidity by the powder fluidity test (funnel test) was performed on the obtained crystal nucleating agent for polyolefin resins. Table 3 shows the result.

Comparative Example 6

The bulk density of PDBN in a powder state before granulation was measured. Table 3 shows the result. Subsequently, the evaluation of the powder fluidity by the powder fluidity test (funnel test) was performed as in the examples. Table 3 shows the result.

Examples 33 to 38

The granular crystal nucleating agent for polyolefin resins of the present invention was obtained as in Example 1, except that CDBS alone was used as the crystal nucleating agent for polyolefin resins instead of DMDBS.

The diameter of the granulation product was measured using a caliper, and was within a range of 0.7 to 1.2 mm.

The aerated bulk density, packed bulk density, and powdering rate of the obtained granular crystal nucleating agent for polyolefin resins were measured. Table 4 shows the results. Subsequently, the evaluation of the powder fluidity by the powder fluidity test (funnel test) was performed on the obtained granular crystal nucleating agent for polyolefin resins. Table 4 shows the result.

Comparative Example 7

Using CDBS alone without blending a compound having a binder effect, extrusion granulation was performed as in Example 1 in an attempt to produce a granular crystal nucleating agent for polyolefin resins. Though slight granulation was observed, the mixture was mostly in a powder state and the granulated part was very fragile and substantially cannot be treated as a granule. Accordingly, classification or like operation was not performed and it was taken as a crystal nucleating agent for polyolefin resins outside the present invention as it was.

The aerated bulk density, packed bulk density, and powdering rate of the obtained crystal nucleating agent for polyolefin resins were measured. Table 4 shows the results.

Subsequently, the evaluation of the powder fluidity by the powder fluidity test (funnel test) was performed on the obtained crystal nucleating agent for polyolefin resins. Table 4 shows the result.

Comparative Example 8

The bulk density of CDBS in a powder state before granulation was measured. Table 4 shows the result. Subsequently, the evaluation of the powder fluidity by the

TABLE 3

| | Example | | | | | | | | Comparative Example | |
|---|---|---|---|---|---|---|---|---|---|---|
| | 25 | 26 | 27 | 28 | 29 | 30 | 31 | 32 | 5 | 6 |
| Composition in step (i) (parts by weight) | | | | | | | | | | |
| PDBN | 60 | 50 | 60 | 50 | 60 | 50 | 60 | 50 | 100 | — |
| Methanol | 40 | 50 | 28 | 35 | 20 | 25 | 12 | 15 | — | — |
| Water | — | — | 12 | 15 | 20 | 25 | 28 | 35 | — | — |
| (1) Characteristics of crystal nucleating agent | | | | | | | | | | |
| Aerated bulk density (g/cm$^3$) | 0.41 | 0.42 | 0.40 | 0.41 | 0.40 | 0.41 | 0.40 | 0.41 | 0.21 | 0.21 |
| Packed bulk density (g/cm$^3$) | 0.45 | 0.45 | 0.43 | 0.43 | 0.43 | 0.44 | 0.42 | 0.43 | 0.34 | 0.28 |
| Powdering ratio (%) | 3.2 | 1.3 | 14.7 | 4.4 | 10.5 | 6.3 | 19.0 | 7.9 | — | — |
| Angle of repose (degrees) | 38 | 37 | 39 | 38 | 38 | 38 | 39 | 38 | 47 | 49 |
| Powder fluidity test | Excellent | Excellent | Excellent | Excellent | Excellent | Excellent | Excellent | Excellent | Poor | Poor |
| (2) Evaluation of molded article | | | | | | | | | | |
| Haze value | 7.9 | 8.0 | 7.9 | 7.9 | 8.1 | 7.9 | 7.9 | 7.9 | 8.0 | 7.9 |
| Evaluation of white spots | Excellent | Excellent | Excellent | Excellent | Excellent | Good | Excellent | Excellent | Poor | Excellent | powder fluidity test (funnel test) was performed as in the examples. Table 4 shows the result.

by the powder fluidity test (funnel test) and sieve analysis was performed. Table 5 shows the results.

TABLE 4

|  | Example | | | | | | Comparative Example | |
|---|---|---|---|---|---|---|---|---|
|  | 33 | 34 | 35 | 36 | 37 | 38 | 7 | 8 |
| Composition in step (i) (parts by weight) | | | | | | | | |
| CDBS | 60 | 50 | 60 | 50 | 60 | 50 | 100 | — |
| Methanol | 40 | 50 | 28 | 35 | 20 | 25 | — | — |
| Water | — | — | 12 | 15 | 20 | 25 | — | — |
| (1) Characteristics of crystal nucleating agent | | | | | | | | |
| Aerated bulk density (g/cm$^3$) | 0.42 | 0.41 | 0.40 | 0.40 | 0.40 | 0.42 | 0.22 | 0.21 |
| Packed bulk density (g/cm$^3$) | 0.45 | 0.46 | 0.42 | 0.43 | 0.44 | 0.45 | 0.34 | 0.30 |
| Powdering ratio (%) | 4.9 | 1.7 | 13.9 | 4.6 | 10.2 | 6.7 | — | — |
| Angle of repose (degrees) | 37 | 37 | 39 | 38 | 38 | 38 | 48 | 49 |
| Powder fluidity test | Excellent | Excellent | Excellent | Excellent | Excellent | Excellent | Poor | Poor |
| (2) Evaluation of molded article | | | | | | | | |
| Haze value | 7.8 | 7.9 | 7.9 | 7.8 | 7.8 | 7.8 | 8.1 | 7.8 |
| Evaluation of white spots | Excellent | Excellent | Good | Excellent | Good | Excellent | Poor | Excellent |

As obvious from the comparison of the results between the examples and the comparative examples in Tables 1 to 4, the granular crystal nucleating agent for polyolefin resins of the present invention is significantly improved in fluidity that has been a problem and remarkably contributes to the improvement of the productivity. The results of the examples and comparative examples in Tables 1 to 4 show that the granular crystal nucleating agent for polyolefin resins of the present invention has very excellent dispersibility or solubility in resin to solve the conventional problem of the dispersibility or solubility in resin. Thus, the obtained polyolefin resin molded article is not likely to suffer problems such as white spots and has very high transparency, being very useful for various applications.

Example 39

DMDBS (GELOL DXR available from New Japan Chemical Co., Ltd., average particle size: 5 μm) as the starting powder of a crystal nucleating agent for polyolefin resins was continuously fed to a compression roll part of a roll-type compression granulator "Compacting machine HMS-25" available from Hosokawa Micron Corporation to be dry-compressed at room temperature under the conditions of a roll pressure of 10 MPa and a roll rotation speed of 25 Hz. Thus, a powder-containing flaky crystal nucleating agent (compression product of DMDBS) of the present invention was obtained.

As another embodiment, the powder-containing flaky crystal nucleating agent of the present invention obtained above was crushed using a screen-type fine impact mill "Feather Mill FM-2F" available from Hosokawa Micron Corporation, thereby obtaining a coarse particle-containing powdery crystal nucleating agent (compression product of DMDBS) of the present invention.

According to the particle size distribution measurement, the obtained powdery crystal nucleating agent of the present invention contained coarse particles of 15 μm or larger at a proportion of 63 vol % or higher.

Subsequently, the bulk density and the angle of repose of the obtained powdery crystal nucleating agent of the present invention were measured, and the evaluation of the powder fluidity and secondary aggregation properties respectively by the powder fluidity test (funnel test) and the sieve analysis was performed. Table 5 shows the results.

Example 40

The flaky crystal nucleating agent of the present invention and the powdery crystal nucleating agent of the present invention were obtained as in Example 39, except that the roll pressure was changed to 7.5 MPa. According to the particle size distribution measurement, the obtained powdery crystal nucleating agent of the present invention contained coarse particles of 15 μm or larger at a proportion of 59 vol % or higher.

Subsequently, the bulk density and angle of repose of the obtained powdery crystal nucleating agent of the present invention were measured, and the evaluation of the powder fluidity and secondary aggregation properties respectively by the powder fluidity test (funnel test) and the sieve analysis was performed. Table 5 shows the results.

Example 41

The flaky crystal nucleating agent of the present invention and the powdery crystal nucleating agent of the present invention were obtained as in Example 39, except that the roll pressure was changed to 5.0 MPa. According to the particle size distribution measurement, the obtained powdery crystal nucleating agent of the present invention contained coarse particles of 15 μm or larger at a proportion of 53 vol % or higher.

Subsequently, the bulk density and angle of repose of the obtained powdery crystal nucleating agent of the present invention were measured, and the evaluation of the powder fluidity and the secondary aggregation properties respectively by the powder fluidity test (funnel test) and the sieve analysis were performed. Table 5 shows the results.

Example 42

The powdery crystal nucleating agent of the present invention was obtained as in Example 39, except that the rotation speed of the roll was changed to 20 Hz. The obtained crystal nucleating agent of the present invention was powdery and therefore subjected to the fluidity test without being crushed.

Subsequently, the bulk density and angle of repose of the obtained powdery crystal nucleating agent of the present invention were measured, and the evaluation of the powder fluidity and the secondary aggregation properties by the powder fluidity test (funnel test) and the sieve analysis were performed. Table 5 shows the results.

Example 43

The flaky crystal nucleating agent of the present invention and the powdery crystal nucleating agent of the present invention were obtained as in Example 40, except that EDBS was used as the starting powder of a crystal nucleating agent for polyolefin resins. According to the particle size distribution measurement, the obtained powdery crystal nucleating agent of the present invention contained coarse particles of 15 μm or larger at a proportion of 65 vol % or higher.

Subsequently, the bulk density and angle of repose of the obtained powdery crystal nucleating agent of the present invention were measured, and the evaluation of the powder fluidity and the secondary aggregation properties respectively by the powder fluidity test (funnel test) was performed. Table 5 shows the results.

Example 44

The powdery crystal nucleating agent of the present invention was obtained as in Example 42, except that EDBS was used as the starting powder of a crystal nucleating agent for polyolefin resins. The obtained crystal nucleating agent of the present invention was powdery and therefore subjected to the fluidity test without being crushed.

Subsequently, the bulk density and angle of repose of the obtained powdery crystal nucleating agent of the present invention were measured, and the evaluation of the powder fluidity and the secondary aggregation properties respectively by the powder fluidity test (funnel test) and the sieve analysis were performed. Table 5 shows the results.

Example 45

The flaky crystal nucleating agent of the present invention and the powdery crystal nucleating agent of the present invention were obtained as in Example 40 except that PDBN was used as the starting powder of a crystal nucleating agent for polyolefin resins. According to the particle size distribution measurement, the obtained powdery crystal nucleating agent of the present invention contained coarse particles of 15 μm or larger at a proportion of 60 vol % or higher.

Subsequently, the bulk density and angle of repose of the obtained powdery crystal nucleating agent of the present invention were measured, and the evaluation of the powder fluidity and the secondary aggregation properties respectively by the powder fluidity test (funnel test) and the sieve analysis were performed. Table 5 shows the results.

Comparative Example 9

The bulk density and angle of repose of raw material DMDBS (starting powder of a crystal nucleating agent for polyolefin resins) before compression treatment were measured, and the evaluation of the powder fluidity and the secondary aggregation properties respectively by the powder fluidity test (funnel test) and the sieve analysis was performed. Table 5 shows the results.

Comparative Example 10

The bulk density and angle of repose of raw material EDBS (starting powder of a crystal nucleating agent for polyolefin resins) before compression treatment were measured, and the evaluation of the powder fluidity and the secondary aggregation properties respectively by the powder fluidity test (funnel test) and the sieve analysis was performed. Table 5 shows the results.

Comparative Example 11

The bulk density and angle of repose of raw material PDBN (starting powder of a crystal nucleating agent for polyolefin resins) before compression treatment were measured, and the evaluation of the powder fluidity and the secondary aggregation properties respectively by the powder fluidity test (funnel test) and the sieve analysis was performed. Table 5 shows the results.

TABLE 5

| | | Example | | | | | | | Comparative Example | | |
|---|---|---|---|---|---|---|---|---|---|---|---|
| | | 39 | 40 | 41 | 42 | 43 | 44 | 45 | 9 | 10 | 11 |
| Type of crystal nucleating agent | | DMDBS | DMDBS | DMDBS | DMDBS | EDBS | EDBS | PDBN | DMDBS | EDBS | PDBN |
| Aerated bulk density | g/cm$^3$ | 0.36 | 0.31 | 0.30 | 0.28 | 0.35 | 0.31 | 0.38 | 0.22 | 0.24 | 0.24 |
| Packed bulk density | g/cm$^3$ | 0.51 | 0.44 | 0.42 | 0.39 | 0.52 | 0.40 | 0.55 | 0.30 | 0.30 | 0.29 |
| Angle of repose | Degrees | 45 | 46 | 48 | 48 | 44 | 48 | 45 | 49 | 49 | 50 |
| Result of sieve analysis | Wt % | 1 | 1 | 2 | 10 | 1 | 11 | 1 | 29 | 27 | 32 |
| Result of evaluating powder fluidity | | Excellent | Excellent | Good | Good | Excellent | Good | Excellent | Poor | Poor | Poor |

Example 46

An amount of 100 parts by weight of a polypropylene random copolymer (MFR=7 g/10 min (load: 2160 g, temperature: 230° C.), R-720 available from Prime Polymer Co., Ltd.) as a polyolefin resin, 0.2 parts by weight of the powdery crystal nucleating agent (compression product of DMDBS) obtained in Example 39 as a crystal nucleating agent, and 0.05 parts by weight of calcium stearate (available from Nitto Kasei Co., Ltd., product name: "Ca-St"), 0.05 parts by weight of tetrakis[methylene-3-(3,5-di-tert-butyl-4-hydroxyphenyl)propionate]methane (available from BASF Japan Ltd., product name: "IRGANOX1010"), and 0.05 parts by weight of tetrakis(2,4-di-tert-butylphenyl) phosphite (available from BASF Japan Ltd., product name: "IRGAFOS168") as other additives were dry-blended. The dry-blended mixture was melted and mixed using a single screw extruder (VS-20 available from Tanabe Plastics Machinery Co., Ltd.) at a barrel temperature of 240° C., and the extruded strands were cooled and cut using a pelletizer. Thus, a polyolefin resin composition was prepared.

Next, the obtained polyolefin resin composition was molded using an injection molding apparatus (NS40-5A available from Nissei Plastic Industrial Co., Ltd.) under the conditions of an injection molding temperature (heating temperature) of 240° C. and a die temperature (cooling temperature) of 40° C. to provide a 1-mm-thick polyolefin resin molded article and a 2-mm-thick polyolefin resin molded article.

The haze values of the obtained molded articles as evaluation samples were measured. Table 6 shows the results. Subsequently, the visual evaluation of white spots in the molded articles by the above method was performed. Table 6 shows the results.

Example 47

A polyolefin resin composition and polyolefin resin molded articles were obtained as in Example 46, except that the powdery crystal nucleating agent (compression product of DMDBS) of the present invention obtained in Example 40 was used as the crystal nucleating agent. The haze values of the obtained molded articles were measured. Table 6 shows the results. Subsequently, the visual evaluation of white spots in the molded articles by the above method was performed. Table 6 shows the results.

Example 48

A polyolefin resin composition and polyolefin resin molded articles were obtained as in Example 46, except that the powdery crystal nucleating agent (compression product of DMDBS) of the present invention obtained in Example 41 was used as the crystal nucleating agent. The haze values of the obtained molded articles were measured. Table 6 shows the results. Subsequently, the visual evaluation of white spots in the molded articles by the above method was performed. Table 6 shows the results.

Example 49

A polyolefin resin composition and polyolefin resin molded articles were obtained as in Example 46, except that the powdery crystal nucleating agent (compression product of DMDBS) of the present invention obtained in Example 42 was used as the crystal nucleating agent. The haze values of the obtained molded articles were measured. Table 6 shows the results. Subsequently, the visual evaluation of white spots in the molded articles by the above method was performed. Table 6 shows the results.

Example 50

A polyolefin resin composition and polyolefin resin molded articles were obtained as in Example 46, except that the powdery crystal nucleating agent (compression product of EDBS) of the present invention obtained in Example 43 was used as the crystal nucleating agent. The haze values of the obtained molded articles were measured. Table 6 shows the results. Subsequently, the visual evaluation of white spots in the molded articles by the above method was performed. Table 6 shows the results.

Example 51

A polyolefin resin composition and polyolefin resin molded articles were obtained as in Example 46, except that the powdery crystal nucleating agent (compression product of EDBS) of the present invention obtained in Example 44 was used as the crystal nucleating agent. The haze values of the obtained molded articles were measured. Table 6 shows the results. Subsequently, the visual evaluation of white spots in the molded articles by the above method was performed. Table 6 shows the results.

Example 52

A polyolefin resin composition and polyolefin resin molded articles were obtained as in Example 46, except that the powdery crystal nucleating agent (compression product of PDBN) of the present invention obtained in Example 45 was used as a crystal nucleating agent. The haze values of the obtained molded articles were measured. Table 6 shows the results. Subsequently, the visual evaluation of white spots in the molded articles by the above method was performed. Table 6 shows the results.

TABLE 6

|  | Example | | | | | | |
| --- | --- | --- | --- | --- | --- | --- | --- |
|  | 46 | 47 | 48 | 49 | 50 | 51 | 52 |
| Type of crystal nucleating agent | DMDBS | DMDBS | DMDBS | DMDBS | EDBS | EDBS | PDBN |
| Haze value | 9 | 8 | 8 | 7 | 10 | 11 | 7 |
| Result of evaluating white spots | Good | Excellent | Excellent | Excellent | Excellent | Excellent | Excellent |

The results in Table 5 show that the compression-treated crystal nucleating agents of the present invention (Examples 39 to 45) have significantly increased bulk densities compared to the crystal nucleating agents not subjected to the compression treatment (Comparative Examples 9 to 11). The results of the sieve analysis show that the compression treatment remarkably improved the secondary aggregation properties, and the results of the measurement of the angle of repose and the evaluation of the powder fluidity show that the compression treatment remarkably improved the fluidity. These results show that the use of the crystal nucleating agent of the present invention significantly improves the workability upon blending with a polyolefin resin and during the molding after the blending.

The results in Table 6 show that the polyolefin resin composition prepared using the compression-treated crystal nucleating agent of the present invention and its molded article are not likely to suffer conventional disadvantages caused by a non-dispersed matter or a non-dissolved matter, such as white spots, to exhibit very excellent properties as a transparent crystal nucleating agent.

INDUSTRIAL APPLICABILITY

The crystal nucleating agent of the present invention has remarkably better fluidity and is usable for various applications as a crystal nucleating agent having very high fluidity.

In the case of the crystal nucleating agent of the present invention, the dispersibility or solubility in polyolefin resins, which has been a problem of conventional crystal nucleating agents, is at a level not causing a practical problem and allows the use of the crystal nucleating agent without problems in terms of the properties of the resulting molded article. Accordingly, the crystal nucleating agent of the present invention can remarkably contribute to the improvement of the productivity or the like in various applications. The resulting polyolefin resin molded article is not likely to suffer disadvantages such as white spots caused by a non-dispersed matter or non-dissolved matter of the crystal nucleating agent and is excellent in optical characteristics (e.g., transparency) and mechanical characteristics (e.g., impact resistance) to be usable for various applications including automobile parts, electric parts, machine components, commodities, cases for cloths or the like, and containers for food or the like. In particular, in medical applications where incorporation of unwanted additives or the like should be avoided, the present invention provides a technique that is greatly expected to be utilized as a technique capable of improving the fluidity without addition of additives.

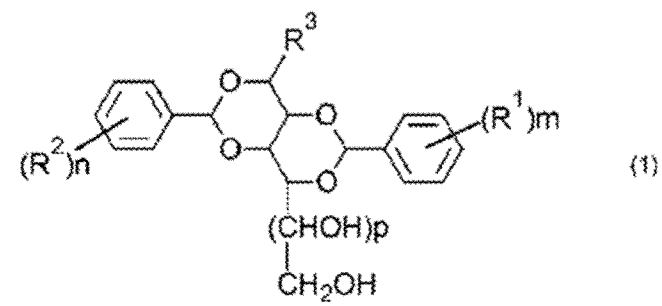

The invention claimed is:

1. A crystal nucleating agent for polyolefin resins, the crystal nucleating agent having an aerated bulk density within a range of 0.25 to 0.50 g/cm³ and a packed bulk density within a range of 0.35 to 0.80 g/cm³, wherein the crystal nucleating agent for polyolefin resins is a granule obtained by preparing a mixture containing a starting powder of the crystal nucleating agent for polyolefin resins and a compound having a binder effect, extrusion-granulating the mixture, and removing the compound having a binder effect from the extrusion-granulation product, and wherein the crystal nucleating agent for polyolefin resins consists of a diacetal compound represented by the following formula (1):

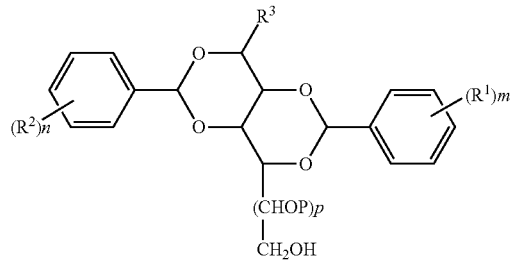

(1)

wherein $R^1$ and $R^2$ are the same as or different from each other and each represent a hydrogen atom, a C1-C4 linear or branched alkyl group, a C1-C4 linear or branched alkoxy group, a C1-C4 linear or branched alkoxy carbonyl group, or a halogen atom; $R^3$ represents a hydrogen atom, a C1-C4 linear or branched alkyl group, a C2-C4 linear or branched alkenyl group, or a C1-C4 linear or branched hydroxy alkyl group; m and n each represent an integer of 1 to 5; p represents 0 or 1; and two $R^1$s optionally bind to each other to form a tetralin ring together with a benzene ring to which they are bonded and two $R^2$s optionally bind to each other to form a tetralin ring together with a benzene ring to which they are bonded.

2. The crystal nucleating agent for polyolefin resins according to claim 1, wherein an angle of repose is 48 degrees or smaller.

3. The crystal nucleating agent for polyolefin resins according to claim 1, wherein, in the formula (1), $R^1$ and $R^2$ are the same as or different from each other and each represent a methyl group or an ethyl group, $R^3$ represents a hydrogen atom, m and n each represent an integer of 1 or 2, and p represents 1.

4. The crystal nucleating agent for polyolefin resins according to claim 1, wherein, in the formula (1), $R^1$ and $R^2$ are the same as or different from each other and each represent a propyl group or a propoxy group, $R^3$ represents a propyl group or a propenyl group, m and n each represent 1, and p represents 1.

5. The crystal nucleating agent for polyolefin resins according to claim 1, wherein a powdering rate is 40% or lower.

6. The crystal nucleating agent for polyolefin resins according to claim 1, wherein the granule has a cylindrical shape with a diameter within a range of 0.5 to 5.0 mm.

7. A method for improving the fluidity of a crystal nucleating agent for polyolefin resins, comprising adjusting the nucleating agent to have an aerated bulk density within a range of 0.25 to 0.50 g/cm³, a packed bulk density within a range of 0.3 to 0.80 g/cm³, and a powdering rate of 40% or lower, wherein the crystal nucleating agent for polyolefin resins is a granule obtained by preparing a mixture containing a starting powder of the crystal nucleating agent for polyolefin resins and a compound having a binder effect, extrusion-granulating the mixture, and removing the compound having a binder effect from the extrusion-granulation product, and wherein the crystal nucleating agent for polyolefin resins consists of a diacetal compound represented by the following formula (1):

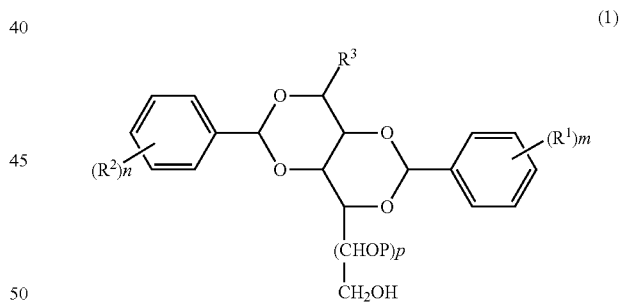

(1)

wherein $R^1$ and $R^2$ are the same as or different from each other and each represent a hydrogen atom, a C1-C4 linear or branched alkyl group, a C1-C4 linear or branched alkoxy group, a C1-C4 linear or branched alkoxy carbonyl group, or a halogen atom; $R^3$ represents a hydrogen atom, a C1-C4 linear or branched alkyl group, a C2-C4 linear or branched alkenyl group, or a C1-C4 linear or branched hydroxy alkyl group; m and n each represent an integer of 1 to 5; p represents 0 or 1; and two $R^1$s optionally bind to each other to form a tetralin ring together with a benzene ring to which they are bonded and two $R^2$s optionally bind to each other to form a tetralin ring together with a benzene ring to which they are bonded.

* * * * *

UNITED STATES PATENT AND TRADEMARK OFFICE
CERTIFICATE OF CORRECTION

PATENT NO. : 11,634,427 B2
APPLICATION NO. : 16/321775
DATED : April 25, 2023
INVENTOR(S) : Shohei Iwasaki et al.

Page 1 of 2

It is certified that error appears in the above-identified patent and that said Letters Patent is hereby corrected as shown below:

In the Claims

At Column 37, Claim number 1, Line numbers 40-53:
The formula (1)

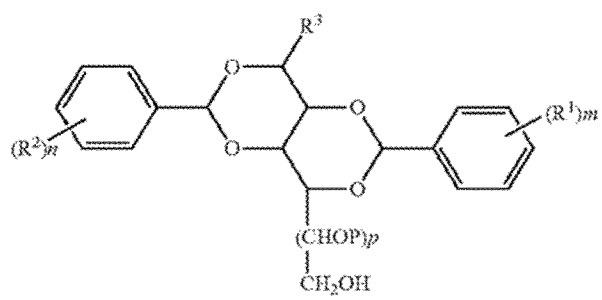

Should read:

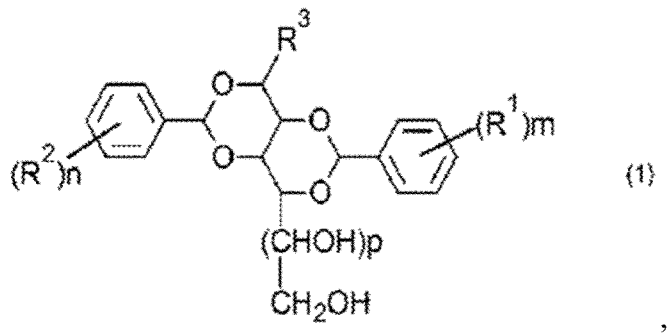

Signed and Sealed this
Twenty-seventh Day of June, 2023

Katherine Kelly Vidal
*Director of the United States Patent and Trademark Office*

CERTIFICATE OF CORRECTION (continued)
U.S. Pat. No. 11,634,427 B2

At Column 38, Claim number 7, Line numbers 40-52:
The formula (1)

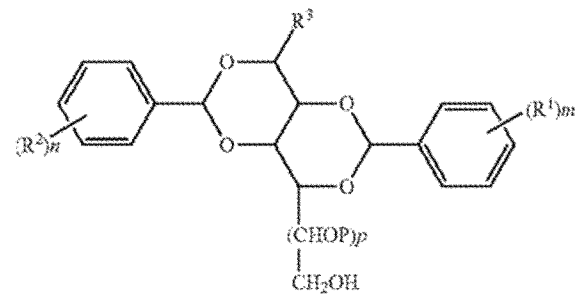

Should read: